(12) United States Patent
Lippard et al.

(10) Patent No.: US 7,488,820 B2
(45) Date of Patent: Feb. 10, 2009

(54) NAPHTHOFLUORESCEIN-BASED METAL SENSORS, AND METHODS OF MAKING AND USING THE SAME

(75) Inventors: Stephen J. Lippard, Cambridge, MA (US); Christopher J. Chang, Berkeley, CA (US); Elizabeth M. Nolan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 397 days.

(21) Appl. No.: 11/039,396

(22) Filed: Jan. 19, 2005

(65) Prior Publication Data

US 2005/0186555 A1   Aug. 25, 2005

Related U.S. Application Data

(60) Provisional application No. 60/546,052, filed on Feb. 19, 2004, provisional application No. 60/537,121, filed on Jan. 19, 2004.

(51) Int. Cl.
*C07D 257/02* (2006.01)
*C07D 405/00* (2006.01)
*C07D 311/88* (2006.01)

(52) U.S. Cl. .................. 540/474; 546/256; 549/225

(58) Field of Classification Search .................. 549/223, 549/224, 225; 546/282.7
See application file for complete search history.

(56) References Cited

U.S. PATENT DOCUMENTS

| 1,194,380 | A |   | 8/1916 | Hagenbach |   |
|---|---|---|---|---|---|
| 4,945,171 | A |   | 7/1990 | Haugland et al. |   |
| 5,624,847 | A | * | 4/1997 | Lakowicz et al. | 436/68 |
| 5,648,269 | A | * | 7/1997 | Lakowicz et al. | 436/68 |
| 6,617,445 | B2 |   | 9/2003 | Benson et al. |   |

OTHER PUBLICATIONS

Lakowicz et al Anal. Chem. 1993, 65, 1668-1674.*
F. Zaragoza Dorwald "Side Reactions in Organic Synthesis: A Guide to Successful Synthesis Design" 2005, Wiley-VCH GmbH and Co. KGaA, Wienheim.*
International Search Report mailed on Oct. 12, 2005.

* cited by examiner

*Primary Examiner*—Rita J. Desai
*Assistant Examiner*—John Mabry
(74) *Attorney, Agent, or Firm*—Foley Hoag LLP

(57) ABSTRACT

The present invention is directed, in part, to naphthofluorescein-based ligands for detection of metal ions, and methods of making and using the same.

11 Claims, 10 Drawing Sheets naphthoxyquinone        phenoxynaphthoquinone

NAPHTHOFLUORESCEIN-BASED METAL SENSORS, AND METHODS OF MAKING AND USING THE SAME

RELATED APPLICATIONS

This application claims the benefit of priority to U.S. Provisional Patent Application Ser. No. 60/537,121, filed Jan. 19, 2004; and U.S. Provisional Patent Application Ser. No. 60/546,052, filed Feb. 19, 2004. Both applications are incorporated by reference.

GOVERNMENT SUPPORT

The subject invention was made in part with support from the U.S. Government.

BACKGROUND OF THE INVENTION

Fluorescence technology has revolutionized cell biology and many areas of biochemistry. In certain instances, fluorescent molecules may be used to trace molecular and physiological events in living cells. Certain sensitive and quantitative fluorescence detection devices have made fluorescence measurements an ideal readout for in vitro biochemical assays. In addition some fluorescence measurement systems may be useful for determining the presence of analytes in environmental samples. Finally, because certain fluorescence detection systems are rapid and reproducible, fluorescence measurements are often critical for many high-throughput screening applications.

The feasibility of using fluorescence technology for a particular application is often limited by the availability of an appropriate fluorescent sensor. There are a number of features that are desirable in fluorescent sensors, some of which may or may not be present in any particular sensor. First, fluorescent sensors should produce a perceptible change in fluorescence upon binding a desired analyte. Second, fluorescent sensors should selectively bind a particular analyte. Third, to allow concentration changes to be monitored, fluorescent sensors should have a $K_d$ near the median concentration of the species under investigation. Fourth, fluorescent sensors, especially when used intracellularly, should produce a signal with a high quantum yield. Fifth, the wavelengths of both the light used to excite the fluorescent molecule (excitation wavelengths) and of the emitted light (emission wavelengths) are often important. If possible, for intracellular use, a fluorescent sensor should have excitation wavelengths exceeding 340 nm to permit use with glass microscope objectives and prevent UV-induced cell damage, and possess emission wavelengths approaching 500 nm to avoid autofluorescence from native substances in the cell and allow use with typical fluorescence microscopy optical filter sets. Finally, ideal sensors should allow for passive and irreversible loading into cells.

The importance of metals in biological systems and the general difficulty in measuring metals in living cells makes metal detection a particularly desirable field for the use of fluorescence technology. As one example, zinc is a vital component in many cellular processes. Although the traditional study of the bioinorganic chemistry of $Zn^{2+}$ has focused on structural and enzymatic functions in proteins, the neurobiology of $Zn^{2+}$ has been gaining attention. Whereas most $Zn^{2+}$ in biological systems is tightly bound in proteins and enzymes, a pool of free $Zn^{2+}$ has been imaged in cells. Subnanomolar concentrations of $Zn^{2+}$ have been detected in undifferentiated mammalian cells, and higher concentrations, approaching 300 μM, have been imaged in the mossy fiber terminals of the hippocampus. The $Zn^{2+}$ ion has the ability to modulate a variety of ion channels, may play a role in neuronal death during seizures, is pertinent to neurodegenerative disorders, and may be vital to neurotransmission and long-term potentiation.

Although $Zn^{2+}$ is critical to cellular processes, excess zinc ions may be toxic. The levels of $Zn^{2+}$ in the brain and other parts of the body are believed to be regulated by three related $Zn^{2+}$ transport proteins (ZnT-1, ZnT-2, and ZnT-3) and by metallothioneins (MTs), including MT-III and MT-IV which are expressed mainly in the brain. ZnTs and MTs are probably responsible for distributing the required $Zn^{2+}$ to proteins and enzymes, and minimizing the amounts of free $Zn^{2+}$ present in cells. In nerve cells, however, free $Zn^{2+}$ is available for neurological functions because $Zn^{2+}$ can be released from synaptic vesicles and can enter cells through voltage-dependent $Ca^{2+}$ channels. Despite the abundance of research, many aspects of ionic $Zn^{2+}$ in neurobiology remain unclear due to the limited detection methods currently available.

Because metal ion levels may be critical to normal cellular function, a number of diseases may result from, or may be caused by, errors in metabolism of a particular metal ion in the affected individual. For example, abnormal zinc metabolism has been found in some Alzheimer's patients, and low levels of zinc are associated with various behavioral disorders. Diagnosis of errors in such metal ion metabolism may be facilitated by the subject invention.

SUMMARY OF THE INVENTION

In one aspect, the present invention is directed to naphthofluorescein-based compounds and ligands, and methods of making and using the same. The present invention provides in part structures derived from naphthofluorescein that may readily be diversified using techniques known to those of skill in the art to prepare a variety of naphthofluorescein-based ligands having Lewis base functionalities to allow for coordination to metal ions, targets and other analytes of interest.

For example, in certain embodiments, the present invention is directed to a naphthofluorescein-based ligand that is capable of coordinating to a metal ion, whereupon such coordination, a fluorescent property of said ligand changes in an amount sufficient to allow the metal ion to be detected. The detection means is usually fluorescence spectroscopy. By "naphthofluorescein-based" for this example, it is meant the ligand contains the following structure, a derivative thereof or a substituted version thereof:

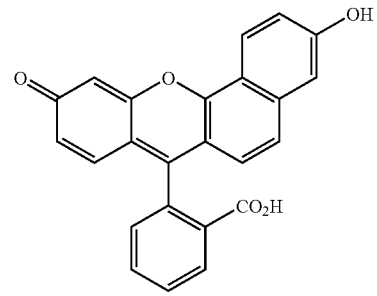

The subject compositions, and methods of making and using the same, may achieve a number of desirable results and features, one or more of which (if any) may be present in any particular embodiment of the present invention: (i) naphthofluorescein-based ligands that bind metal ions with a concomitant change in the fluorescence properties of the ligand; (ii)

scaffold molecules with latent functionality that allow for a variety of naphthofluorescein-based ligands to be prepared; (iii) naphthofluorescein-based ligands that selectively bind a metal ion; (iii) naphthofluorescein-based ligands that have a $K_d$ near the median concentration of the metal ion under investigation allowing for concentrations of the metal ion to be determined; (iv) naphthofluorescein-based ligands that exhibit a high quantum yield upon complexation of a metal ion; (v) excitation wavelengths for naphthofluorescein-based ligands that exceed 340 nm and emission wavelengths that approach 500 nm; (vi) naphthofluorescein-based ligands that are capable of in vivo use, and possibly also loading into cells; and (vii) upon binding a metal of interest, the subject ligands exhibit a shift in emission wavelength, which may be used for among other things visualizing concentration fluctuations and spatial distributions.

In one aspect, the present invention is directed to naphthofluorescein-based ligands with the following structure:

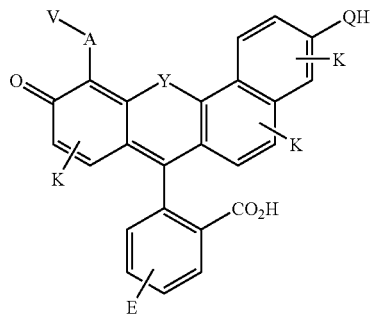

wherein, as described in greater detail below, A is a moiety having one or more carbon atoms; Q is O, NR' or S, wherein R' is —H or an alkyl, optionally substituted; K and E are optionally one or more substituents of the indicated aromatic ring that do not materially alter the fluorescence of the ligand as described below; V is a Lewis base capable of forming one or more coordination bonds with a metal ion; Y is O, S, Se, NR, or $C(CH_3)_3$, wherein R is an alkyl and R and the methyl groups of $C(CH_3)_2$ are optionally substituted; and in each instance substituted derivatives thereof.

One exemplary naphthofluorescein-based ligand, optionally substituted, has the following structure:

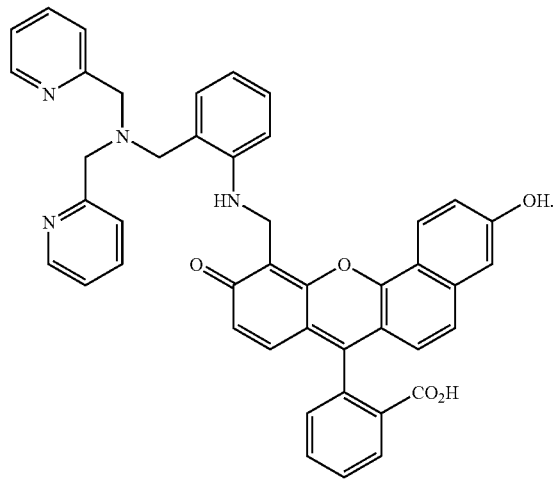

The naphthofluorescein-based ligand depicted above, hereinafter referred to as ZNP1 (Zin-naphthopyr 1), is capable of single-excitation, dual-emission ratiometric imaging of $Zn^{2+}$, including intracellular $Zn^{2+}$. The molecule has excitation and emission maxima in the visible range, selectivity for $Zn^{2+}$ over metal ions such as $Na^+$, $K^+$, $Ca^{2+}$, and $Mg^{2+}$, and a dissocation constant ($K_d$) for $Zn^{2+}$ of less than 1 nM.

Another exemplary naphthofluorescein-based ligand, optionally substituted, has the following structure:

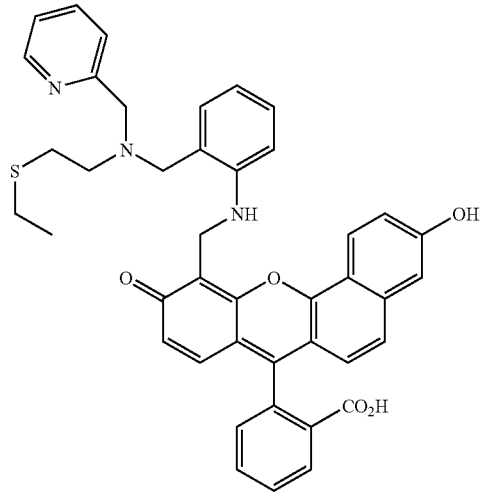

The naphthofluorescein-based ligand depicted above, hereinafter referred to as MS4, is capable of single-excitation, dual-emission ratiometric imaging of $Hg^{2+}$. The molecule has excitation and emission maxima in the visible range, selectivity for $Hg^{2+}$ over metal ions such as $Na^+$, $Ca^{2+}$, and $Mg^{2+}$.

Another exemplary naphthofluorescein-based ligand, optionally substituted, has the following structure:

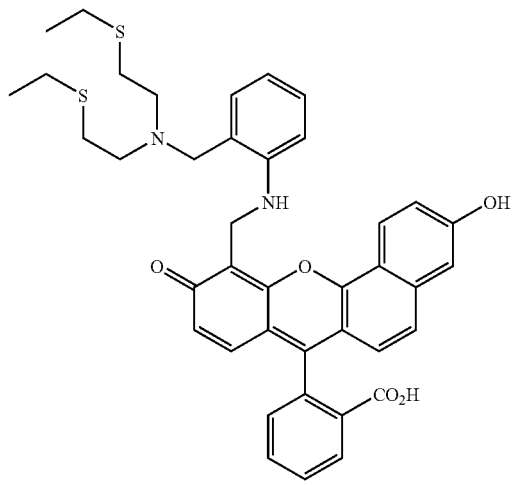

The naphthofluorescein-based ligand depicted above, hereinafter referred to as MS5, is capable of single-excitation, dual-emission ratiometric imaging of $Hg^{2+}$. The molecule has excitation and emission maxima in the visible range, selectivity for $Hg^{2+}$ over metal ions such as $Na^+$, $Ca^{2+}$, and $Mg^{2+}$.

In certain embodiments, a single subject ligand may detect more than one metal ion or other analyte of interest.

In other embodiments, the naphthofluorescein-based ligands of the present invention have the structures described in the figures, the detailed description and the claims below, all of which structures are hereby incorporated by reference in their entirety into this Summary to describe the present invention.

In another aspect, the subject naphthofluorescein-based compounds may be attached to a targeting moiety to direct the ligand to a particular target. For instance, targeting of the subject ligands may allow for detection, and, optionally, quantification of the concentration of, metal ions at a target cell of interest in vivo.

In another aspect, the present invention is directed to coordination complexes comprising the subject naphthofluorescein-based ligands complexed to one or more metal ions.

In another aspect, the present invention provides scaffold compounds that have sites of latent functionality which may be readily diversified into subject naphthofluorescein-based compounds. One non-limiting example of such a scaffold molecule is:

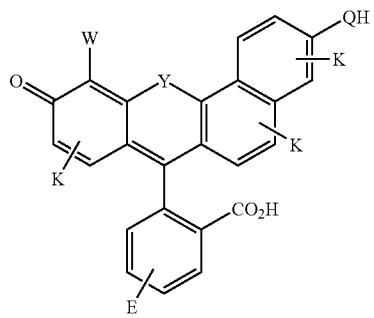

wherein W comprises at least one carbon atom bound to the aromatic ring carbon and wherein W is a site of latent functionality, and all other moieties are as defined above.

Other non-limiting subject scaffolds with latent functionality include:

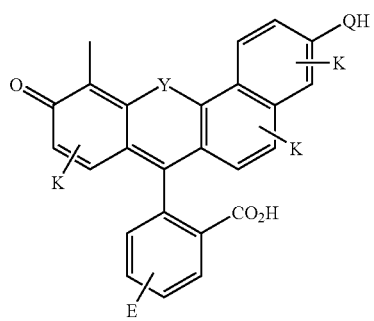

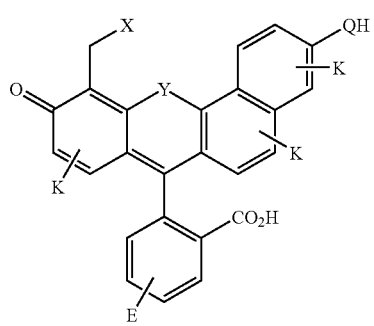

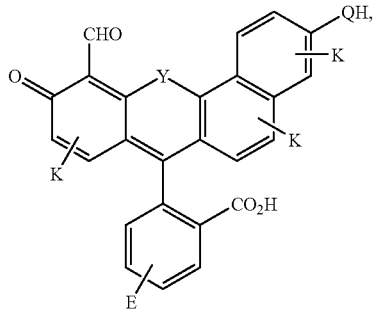

wherein X is halogen.

In another aspect, the present invention provides a number of methods of making the subject compositions, including the subject naphthofluorescein-based ligands, compounds and scaffolds.

In another aspect, the subject invention involves methods of using the subject naphthofluorescein-based ligands, which uses include detecting, and, optionally, quantifying concentrations of, metal ions in a sample. The detection methods rely on the change observed in the fluorescence of the subject naphthofluorescein-based ligands upon complexation with a metal ion. Any change observed, both positive and negative, and including, for example, a change in the emission wavelength, the excitation wavelength, and the quantum yield, may be used to detect metal ion complexation. The methods may be used in vivo to detect changes in intracellular concentrations of metal ions with the appropriate naphthofluorescein-based ligand. In addition, the present inventive methods provide for positive and negative controls.

In another aspect, the present invention is directed to methods of using the subject naphthofluorescein-based ligands for diagnostic purposes. In certain instances, the subject compositions and methods may be used to detect, and, optionally, to quantify the concentration of, a metal ion or other analyte of interest in a patient.

In another aspect, the present invention is directed to methods of using the subject naphthofluorescein-based ligands for determining the presence of analytes in samples, including samples of environmental interest. In certain aspects, such samples may have a pH of approximately 3, 4 5, 6, 7, 8, 9, 10, 11, 12, or higher, or alternatively, when the sample is from a natural source, the pH that is naturally-occurring (e.g. a human tissue or fluid, or a soil or water sample).

In other embodiments, this invention contemplates a kit including subject compositions, and optionally instructions for their use. Uses for such kits include, for example, diagnostic applications.

These embodiments of the present invention, other embodiments, and their features and characteristics, will be apparent from the description, drawings and claims that follow.

DETAILED DESCRIPTION

Definitions

Figure 1:
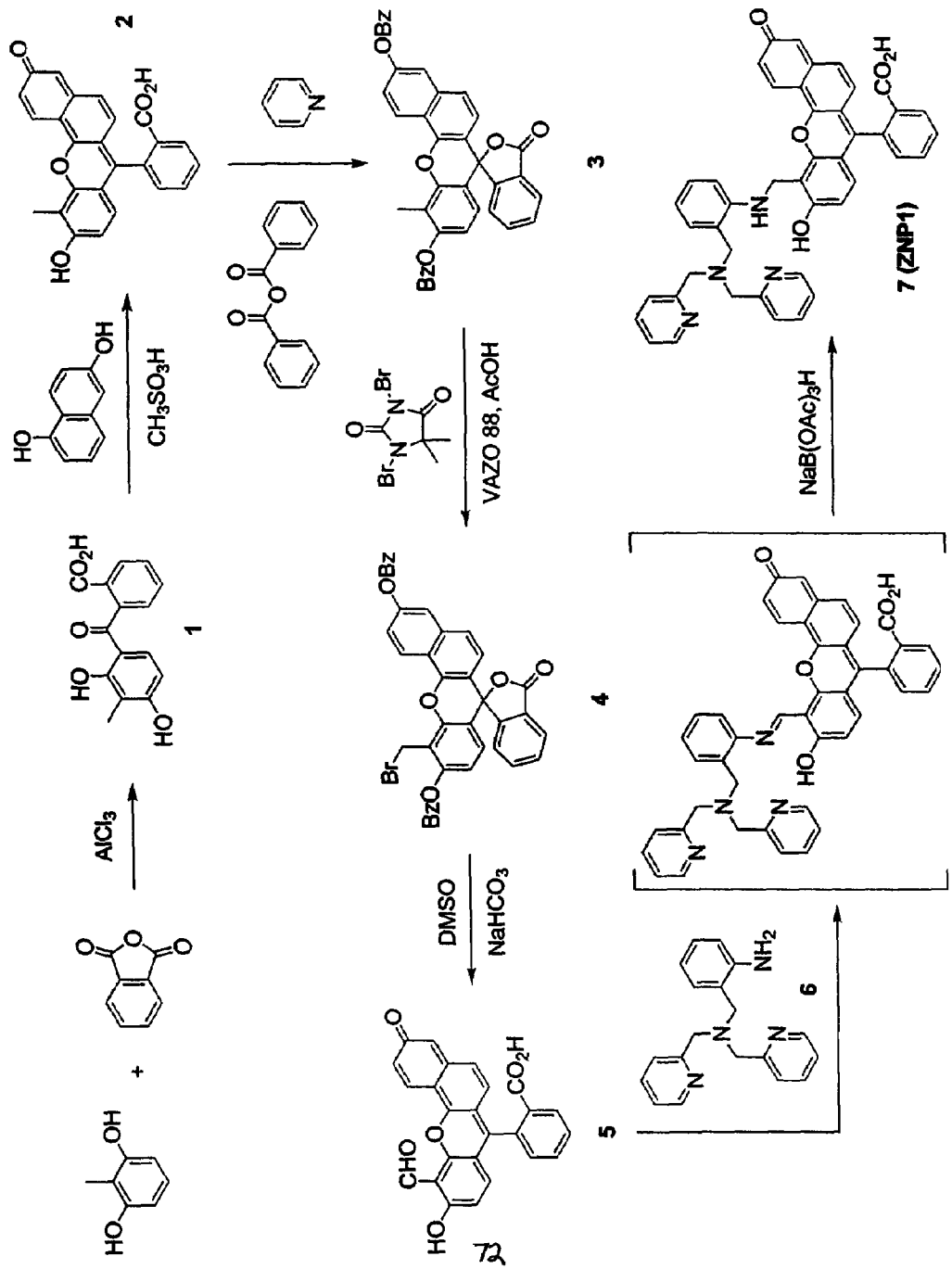
FIG. 1. Synthesis of Zinc-naphthopyr 1, ZNP1.

For convenience, before further description of the present invention, certain terms employed in the specification, examples and appended claims are collected here. These definitions should be read in light of the remainder of the disclosure and understood as by a person of skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used herein to mean "including but not limited to". "Including" and "including but not limited to" are used interchangeably.

The term "chromophore" is art-recognized and that refers to a molecule or part of a molecule that absorbs specific frequencies of light, including ultraviolet light.

The term "fluorophore" refers to a chromophore that fluoresces. Certain fluorophores generally absorb above 300 nm, certain fluorophores generally emit above 300 nm, and certain fluorophores both generally absorb and emit above 300 nm. Alternatively, the threshold may be 350 nm, 400 nm, 425 nm, 450 nm and 500 nm or greater for any particular fluorophore.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below.

The term "label" refers to a composition detectable by spectroscopic, photochemical, biochemical, immunochemical chemical or other means. For example, useful labels include $^{32}P$, chromophores, fluorophores, fluorescent proteins, electron-dense reagents, enzymes (e.g., as commonly used in an ELISA), biotin, dioxigenin, or haptens and proteins for which antisera or monoclonal antibodies are available. A label often generates a measurable signal, such as radioactivity, fluorescent light or enzyme activity, which may in certain instances be used to quantitate the amount of label present.

The term "ligand" is art-recognized and refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "fluorescent ratiometricity" refers to the ratio of excitation amplitudes at two different wavelengths, the ratio of emission amplitudes at two different wavelengths, or the ratio of excitation amplitude at one wavelength to the ratio of emission amplitude at another wavelength (and vice-versa).

The terms "labile" and "non-labile" are art-recognized and are usually used in this context in reference to a ligand bonded to a metal ion. Without intending to limit or modify the definition for the term as it is known in the art, a labile ligand may be understood to be a ligand whose bond to the metal ion is expected to break under certain circumstances.

The terms "Lewis acid" and "Lewis acidic" are art-recognized and refer to chemical moieties which can accept a pair of electrons from a Lewis base as defined above.

The term "fluorescent property" refers to, with respect to a fluorophore, the molar extinction coefficient at an appropriate excitation wavelength, the fluorescence quantum efficiency, the shape of the excitation spectrum or emission spectrum, the excitation wavelength maximum and emission wavelength maximum, the excited state lifetime, or the fluorescence anisotropy. A measurable difference can be determined by determining the amount of any quantitative fluorescent property, e.g., the amount of fluorescence at a particular wavelength, or the integral of fluorescence over the emission spectrum. Fluorescent properties will often be affected by fluorescence resonance energy transfer ("FRET").

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The terms "coordinate bond" or "coordination bond" are art-recognized and refer to an interaction between an electron pair donor and a coordination site on a metal ion leading to an attractive force between the electron pair donor and the metal ion. The use of these terms is not intended to be limiting, in so much as certain coordinate bonds may also be classified as having more or less covalent character (if not entirely covalent character) depending on the nature of the metal ion and the electron pair donor.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "covalently linked" and variations thereof when used in reference to a subject compound refers to the connection of two fluorophores by a cleavable linker, so that before the linker is cleaved, the two fluorophores and the cleavable linker would be understood to be part of the same molecule.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and means a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A metal ion complex is a coordination complex in which the metal ion is a metal ion. In general, the terms "compound," "composition," "agent" and the like discussed herein include complexes, coordination complexes and metal ion complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a coordination complex is charged, in that the metal ion and any Lewis bases in the aggregate are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetraflurorborate, hexafluorophosphate, and monocarboxylates, and dianions such as sulfate. In some cases, coordination complexes themselves may serve as counterions to another coordination complex.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors including theoretical considerations such as kinetic versus thermodynamic effects, as well as the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "cleavable moiety", when used in reference to a subject compound, refers to a moiety that is cleavable by chemical, photochemical, enzymatic or other means to give a fluorophore and a non-fluorophore product when the subject compound is used to measure the presence and/or concentration of a metal ion under suitable conditions. In certain instances, the cleavable linker or moiety is intended to be cleaved once the subject compound has reached the site at which a measurement of metal ion concentration is desired, e.g. a cell or type of tissue or location in a patient.

The term "naturally-occurring", as applied to an object, refers to the fact that an object can be found in nature. For example, an enzyme that is present in an organism that can be isolated from a source in nature and which has not been intentionally modified by man in the laboratory is naturally-occurring.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intended environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be covalently bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and means a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

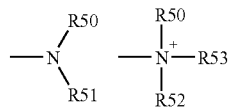

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "ammine" is art-recognized are refers to a compound containing an ammonia moiety or moieties coordinated to a metal ion. The term "ammonia" is art-recognized an refers to an amine group substituted with hydrogens.

The term "acylamino" is art-recognized and refers to a moiety that may be represented by the general formula:

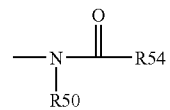

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

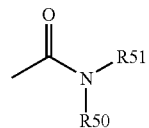

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

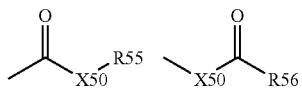

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

$$-\overset{\overset{\displaystyle O}{\|}}{\underset{\underset{\displaystyle O}{\|}}{S}}-OR57$$

in which R57 is an electron pair, hydrogen, alkyl, cycloalkyl, or aryl.

The term "sulfate" is art recognized and includes a moiety that may be represented by the general formula:

$$-O-\overset{\overset{\displaystyle O}{\|}}{\underset{\underset{\displaystyle O}{\|}}{S}}-OR57$$

in which R57 is as defined above.

The term "sulfonamido" is art recognized and includes a moiety that may be represented by the general formula:

$$-\underset{\underset{\displaystyle R50}{|}}{N}-\overset{\overset{\displaystyle O}{\|}}{\underset{\underset{\displaystyle O}{\|}}{S}}-OR56$$

in which R50 and R56 are as defined above.

The term "sulfamoyl" is art-recognized and refers to a moiety that may be represented by the general formula:

$$-\overset{\overset{\displaystyle O}{\|}}{\underset{\underset{\displaystyle O}{\|}}{S}}-N\overset{\displaystyle R50}{\underset{\displaystyle R51}{}}$$

in which R50 and R51 are as defined above.

The term "sulfonyl" is art-recognized and refers to a moiety that may be represented by the general formula:

$$-\overset{\overset{\displaystyle O}{\|}}{\underset{\underset{\displaystyle O}{\|}}{S}}-R58$$

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

$$-\underset{\underset{\displaystyle R58}{}}{\overset{\displaystyle O}{S}}\hspace{-0.5em}\diagup$$

in which R58 is defined above.

The term "phosphoryl" is art-recognized and may in general be represented by the formula:

$$-\overset{\overset{\displaystyle Q50}{\|}}{\underset{\underset{\displaystyle OR59}{|}}{P}}-$$

wherein Q50 represents S or O, and R59 represents hydrogen, a lower alkyl or an aryl. When used to substitute, e.g., an alkyl, the phosphoryl group of the phosphorylalkyl may be represented by the general formulas:

$$-Q51-\overset{\overset{\displaystyle Q50}{\|}}{\underset{\underset{\displaystyle OR59}{|}}{P}}-O- \quad -Q51-\overset{\overset{\displaystyle Q50}{\|}}{\underset{\underset{\displaystyle OR59}{|}}{P}}-O-OR59$$

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

$$-Q51-\overset{\overset{\displaystyle O}{\|}}{\underset{\underset{\displaystyle R50\hspace{0.5em}R51}{N}}{P}}-O- \quad -Q51-\overset{\overset{\displaystyle O}{\|}}{\underset{\underset{\displaystyle R50\hspace{0.5em}R51}{N}}{P}}-OR59$$

wherein Q51, R50, R51 and R59 are as defined above.

The term "phosphonamidite" is art-recognized and may be represented in the general formulas:

$$-Q51-\overset{\overset{\displaystyle R60}{|}}{\underset{\underset{\displaystyle R50\hspace{0.5em}R51}{N}}{P}}-O- \quad -Q51-\overset{\overset{\displaystyle R60}{|}}{\underset{\underset{\displaystyle R50\hspace{0.5em}R51}{N}}{P}}-OR59$$

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* ($2^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59 (McGraw Hill Book Company: New York, 1977). The Hammett constant values are generally negative for electron donating groups (σ(P)=–0.66 for $NH_2$) and positive for electron withdrawing groups (σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives.

The terms "amino acid residue" and "peptide residue" are art-recognized and refer to an amino acid or peptide molecule without the —OH of its carboxyl group.

The term "amino acid residue" further includes analogs, derivatives and congeners of any specific amino acid referred to herein, as well as C-terminal or N-terminal protected amino acid derivatives (e.g. modified with an N-terminal or C-terminal protecting group).

The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed by utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L). Opposite or mixed configurations are acceptable when appropriate to optimize a binding activity.

The term "antibody" is art-recognized and intended to include whole antibodies, e.g., of any isotype (IgG, IgA, IgM, IgE, etc.), and includes fragments thereof which are also specifically reactive with a vertebrate, e.g., mammalian protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

The terms "human monoclonal antibodies" and "humanized" murine antibodies, are art-recognized and refer to monoclonal antibodies "humanized" by genetically recombining the nucleotide sequence encoding the a non-human Fv region (i.e., containing the antigen binding site) or the complementarity-determining regions thereof with the nucleotide sequence encoding at least a human constant domain region and an Fc region, e.g., in a manner similar to that fro mouse disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

"Target" is art-recognized and means a site to which a targeted molecule binds. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). Certain target infectious organisms include those that are drug resistant (e.g., Enterobacteriaceae, Enterococcus, *Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, brain tissue, pancreatic tissue etc.

"Targeting moiety" refers to any molecular structure which assists a molecule in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

The term "bioavailable" is art-recognized and means that a compound the subject invention is in a form that allows for it, or a portion of the amount administered, to be absorbed by, incorporated to, or otherwise physiologically available to a subject or patient to whom it is administered.

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient for diagnostic use of the subject compositions. One of ordinary skill in the art may empirically determine the effective amount of a particular compound without necessitating undue experimentation.

"Small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "modulation" is art-recognized and refers to up regulation (i.e., activation or stimulation), down regulation (i.e., inhibition or suppression) of a response, or the two in combination or apart.

The term "treating" is an art-recognized term which includes curing as well as ameliorating at least one symptom of any condition or disease. Diagnostic applications are also examples of "treating".

A "patient," "subject", or "host" to be treated by the subject method is art-recognized, and means either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The phrase "pharmaceutically acceptable" is art-recognized. In certain embodiments, the term includes subject compounds, pharmaceutical compositions, fluorescein-based ligands and fluorophores and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

The phrases "systemic administration," "administered systemically," "peripheral administration" and "administered peripherally" are art-recognized, and include the administration of a subject composition or other material other than directly into the central nervous system, e.g., by subcutaneous administration, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compounds described herein include compounds which otherwise correspond thereto, and which have the same general properties thereof (such as other fluorophores, with or without Lewis base(s) for coordinating metal ions), wherein one or more simple variations of substituents are made which do not adversely affect the characteristics of the compounds of interest. In general, the compounds of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

Overview

In part, the present invention is directed to naphthofluorescein-based ligands for metal ions. One example of a metal ion that may be the target of such a ligand is zinc. Other metal ions may also be targets for certain subject ligands.

Zinc is an indispensable element for sustaining life and is the second-most abundant transition metal in the human body. Owing to its unique electronic and structural preferences, $Zn^{2+}$ plays a central role in regulating cellular metabolism. Zn2+ is an essential cofactor in all six classes of enzymes, as well as several families of regulatory proteins, including those that control gene expression, DNA repair, and apoptosis.

The physiological importance of $Zn^{2+}$ demands that cells exert strict control over the homeostasis of this ubiquitous metal ion, and most stores of intracellular Zn2+ are tightly bound and serve as structural and/or catalytic components of metalloprotein scaffolds. Nevertheless, histochemical studies reveal that many mammalian organs accumulate pools of labile $Zn^{2+}$ under normal physiological conditions. Prominent examples include the brain, pancreas, and prostate. In addition, alterations of $Zn^{2+}$ homeostasis are implicated in a number of significant human disorders; disrupted patterns of intracellular $Zn^{2+}$ accumulation have been found in patients with Alzheimers' disease, diabetes, and cancer. Despite the far-ranging consequences of $Zn^{2+}$ homeostasis in human physiology and pathology, however, the mechanistic details surrounding intracellular $Zn^{2+}$ accumulation, trafficking, and function remain poorly defined even in the simplest single-cell organisms.

A variety of naphthofluorescein-based compounds, ligands and scaffolds, and methods of using and making the same, are contemplated by the present invention. The term "naphthofluorescein-based" ligand or compound includes references to a "semi-naphthofluorescein" structure. In certain embodiments, the subject ligands form coordination complexes with a variety of metal ions, with on occasion a concomitant change in the fluorescent properties of the resulting metal complex as compared to the uncomplexed ligand. In certain embodiment, such ligands may be used to assay for metal ions, including without limitation those that are often referred to as being spectrophotometrically silent, such as $Zn^{2+}$, and the light metals (e.g., $Li^+$, $Mg^{2+}$, $Ca^{2+}$, etc.). A variety of methods of preparing such ligands and the coordination complexes, of assaying for the binding activity of such ligands, and of using such compositions are also taught by the subject invention. A number of different ligands and metal ions are contemplated for the subject coordination complexes, as set out in more detail below.

Without intending to be limiting or bound to any particular mechanism of action, it is hypothesized that, in certain of the subject naphthofluorescein-based ligands, the hybrid fluorophore can attain two limiting forms (tautomers) with corresponding optical characteristics of the two respective chromophore constitutents. Integration of a metal ion receptor into the π system of the hybrid fluorophore platform should allow analyte binding to influence the ratio of these electronically different tautomers, thus triggering a shift in excitation and/or emission profiles.

Figure 2:
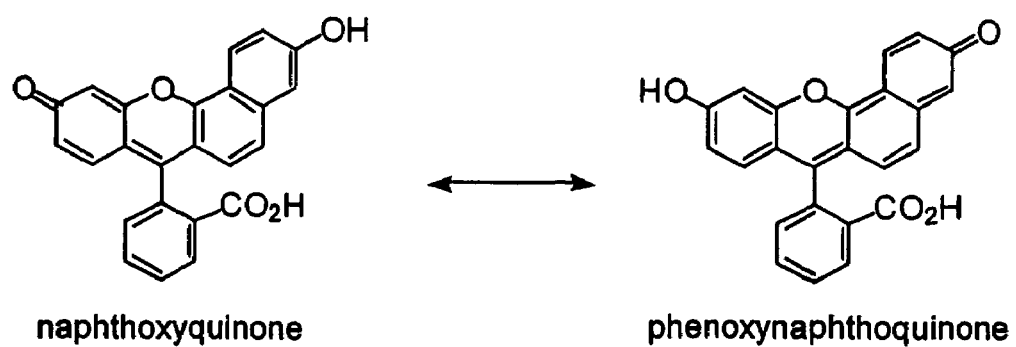
FIG. 2. Two tautomeric forms of the semi-naphthofluorescein fluorophore. The naphthoxyquinone mesomer (left) has fluorescein-like optical properties, and the phenoxynaphthoquinone mesomer (right) shares optical characteristics more akin to naphthofluorescein. Without limitation, and not intending to be bound to a mechanism of action or otherwise, it is hypothesized that the sensing ability of $Zn^{2+}$ by ZNP 1 is achieved through Zn 2+-induced switching between the fluorescein and naphthofluorescein tautomeric forms.

In certain examples of the subject naphthofluorescein-based ligands, the two limiting tautomeric forms are the naphthoxyquinone mesomer, which has fluorescein-like optical properties, and the phenoxynaphthoquinone mesomer, which shares optical characteristics with naphthofluorescein (FIG. 2). Incorporation of a metal binding portion onto such a naphthofluorescein platform affords, in certain embodiments, metal-dependent switching between the fluorescein- and naphthofluorescein-like tautomers. For one naphthofluorescein-based ligand, it is shown that ratiometric fluorescence imaging can then distinguish the relative amounts of these tautomers induced by changes in $Zn^{2+}$ concentration.

Exemplary Naphthofluorescein-based Ligands

In part, the subject invention is directed to the naphthofluorescein-based ligands represented by:

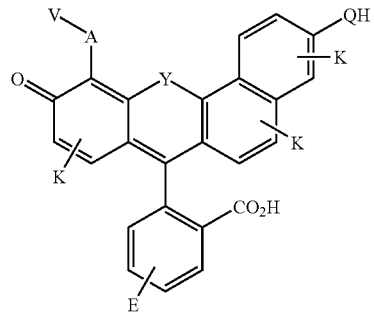

wherein, independently for each occurrence:

A is a chemical moiety having one to about 10 carbon atoms;

Q is O, NR' or S, wherein R' is —H or an alkyl, optionally substituted;

V is a chemical moiety comprising a Lewis base capable of forming one or more coordination bonds with a metal ion;

Y is O, S, Se, NR, or $C(CH_3)_2$, wherein R is an alkyl and R and the methyl groups of $C(CH_3)_2$ are optionally substituted;

K is optionally one or more of the following substituents of the indicated aromatic ring: aliphatic, alkyl, aralkyl, alkenyl, alkynyl, aryl, amine, acyl, acyloxy, acylamino, amido, alkylthio, carbonyl, alkoxyl, sulfonate, sulfate, sulfamoyl, sulfonyl, sulfoxido, selenoalkyl, nitro, halogen, sulfhydryl, cyano, hydroxyl, carbamoyl, sulfonyl and trifluoromethyl; and E is optionally one or more of the following substituents of the indicated aromatic ring: aliphatic, alkyl, aralkyl, alkenyl, alkynyl, aryl, amine, acyl, acyloxy, acylamino, amido, alkylthio, carbonyl, alkoxyl, sulfonate, sulfate, sulfamoyl, sulfonyl, sulfoxido, selenoalkyl, nitro, halogen, sulfhydryl, cyano, hydroxyl, carbamoyl, sulfonyl and trifluoromethyl.

In general, A is any chemical moiety that does not preclude using the resulting naphthofluorescein-based ligand for detection of an analyte of interest, such as a metal ion. In certain embodiments, A has from 1 to 10, or any integer between, of carbon atoms. For example and without limitation, A is one of the following, optionally substituted: —$CH_2$—, —C(=O)—, —C(=S)—, —$CH_2CH_2$—, —$CH_2C$(=O)—, —$CH_2C$(=S)—, and —C(H)=.

In general, K and E are chemical moieties that do not preclude using the resulting naphthofluorescein-based ligand for detection of an analyte of interest. K or E may be any one or more substituents at any of the aromatic ring carbon positions. In certain embodiments each K or E, if present and independently for each occurrence, may be a linear or branched alkyl, alkenyl, linear or branched aminoalkyl, linear or branched acylamino, linear or branched acyloxy, linear or branched alkoxycarbonyl, linear or branched alkoxy, linear or branched alkylaryl, linear or branched hyrdoxyalkyl, linear or branched thioalkyl, acyl, amino, hydroxy, thio, aryloxy, arylalkoxy, hydrogen, alkynyl, halogen, cyano, sulfhydryl, carbamoyl, nitro, trifluoromethyl, amino, thio, lower alkoxy, lower alkylthio, lower alkylamino, nitro, phenoxy, benzyloxy, hydrogen, amine, hydroxyl, alkoxyl, carbonyl, acyl, formyl, sulfonyl and the like.

The identity of K or E may affect the fluorescence properties of the resulting compound, as known to one of skill in the art. A variety of mechanisms may explain the affect of K or E on fluorescence, including, for example, double bond torsion, low energy nσ* levels, "heavy" atoms, weak bonds, photoinduced electron transfer (PET) and electronic energy transfer (EET).

In certain embodiments, K is an electron-withdrawing group that is not a Lewis base, such as the halogens and trifluoromethyl, and in certain embodiments, K is —F or —Cl.

In certain embodiments, E is one or more of amido, carbonyl or halogen.

In certain embodiments, V is capable of forming a bidentate chelating agent consisting of an atom of V donating an electron pair and the oxygen atom of the adjacent hydroxyl group(s) of the ring structure. Alternatively, V itself includes two or more atoms that serve as Lewis bases and are capable of forming bidentate, tridentate, tetradentate or greater chelating agents by themselves or in conjunction with the oxygen atoms of the hydroxyl substituents of the fluorescein structure. In certain embodiments, the atoms that serve to donate electrons for V are nitrogen, oxygen, sulfur or phosphorus.

In general, V contains a Lewis base fragment that is contemplated to encompass numerous chemical moieties having a variety of structural, chemical and other characteristics capable of forming coordination bonds with a metal ion. The types of functional groups capable of forming coordinate complexes with metal ions are too numerous to categorize here, and are known to those of skill in the art. For example, such moieties will generally include functional groups capable of interaction with a metal center, e.g., heteroatoms such as nitrogen, oxygen, sulfur, and phosphorus.

Metal cations are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties which may be included in V include (assuming appropriate modification of them to allow for their incorporation into V and the subject naphthofluorescein-based ligands): amines (primary, secondary, and tertiary) and aromatic amines, amino groups, amido groups, nitro groups, nitroso groups, amino alcohols, nitriles, imino groups, isonitriles, cyanates, isocyanates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable V include those chemical moieties containing at least one Lewis basic nitrogen, sulfur, phosphorous or oxygen atom or a combination of such nitrogen, sulfur, phosphorous and oxygen atoms. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents.

Further examples of Lewis base functionalities suitable for use in V include the following chemical moieties (assuming appropriate modification of them to allow for their incorporation into V and the subject naphthofluorescein-based ligands): amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

Other suitable structural moieties that may be included in V include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates, thiocarboxylate and the like.

Other suitable ligand fragments for use in V include structural moieties that are bidentate ligands, including diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable fragments for use in V include ligand fragments that are tridentate ligands, including 2,5-diiminopyridyl ligands, tripyridyl moieties, triimidazoyl moieties, tris pyrazoyl moieties, and combinations of the above ligands.

Other suitable ligand fragments may consist of amino acids or be formed of oligopeptides and the like.

Because the Lewis basic groups function as the coordination site or sites for the metal cation, in certain embodiments, it may be preferable that the deformability of the electron shells of the Lewis basic groups and the metal cations be approximately similar. Such a relationship often results in a more stable coordination bond. For instance, sulfur groups may be desirable as the Lewis basic groups when the metal cation is a heavy metal. Some examples include the oligopeptides such as glutathione and cysteine, mercapto ethanol amine, dithiothreitol, amines and peptides containing sulfur and the like. Nitrogen containing groups may be employed as the Lewis basic groups when smaller metal ions are the metal. Alternatively, for those applications in which a less stable coordination bond is desired, it may be desirable that the deformability be dissimilar.

Figure 6:
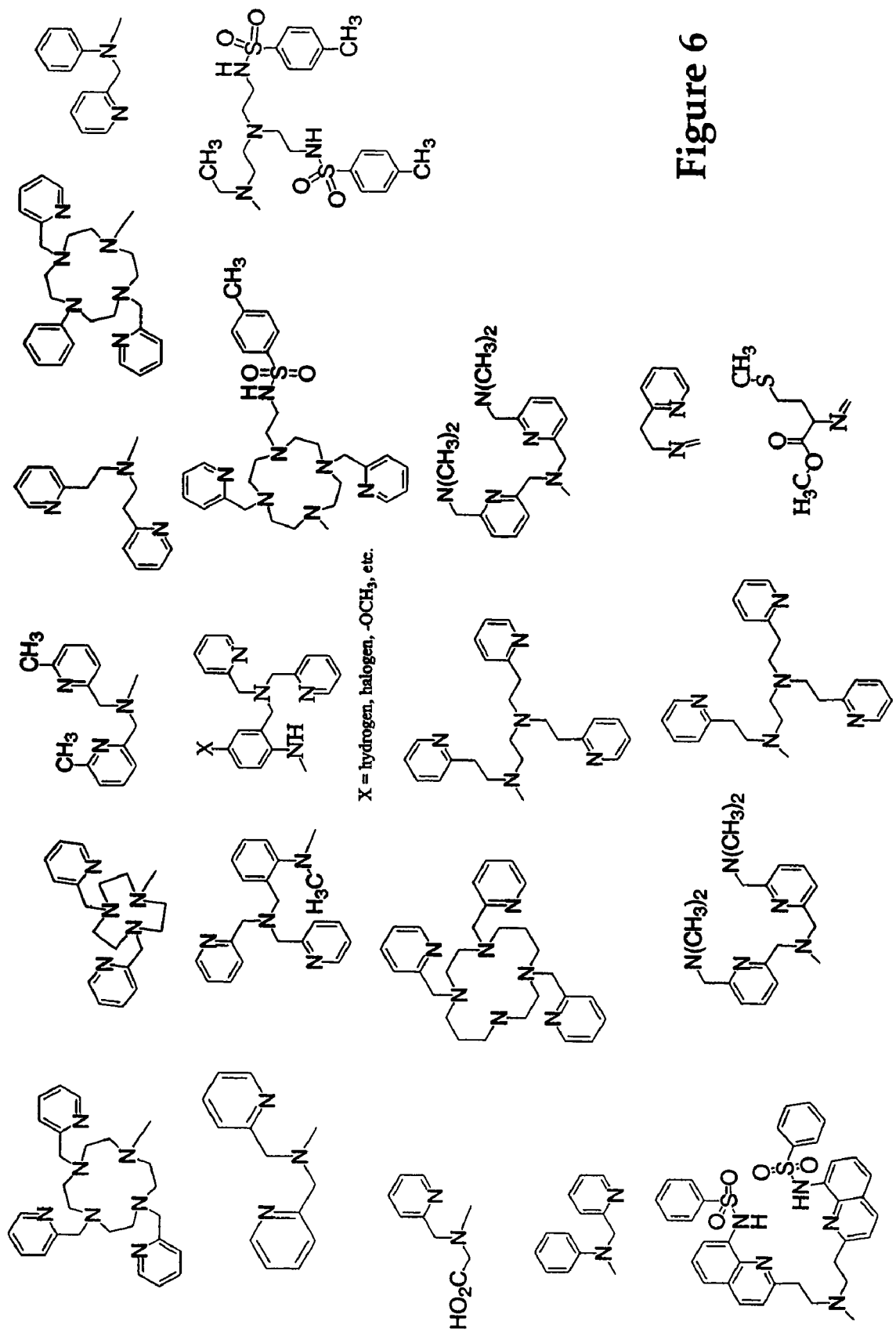
FIG. 6 shows exemplary V for the subject naphthofluorescein-based ligands.
Figure 7:
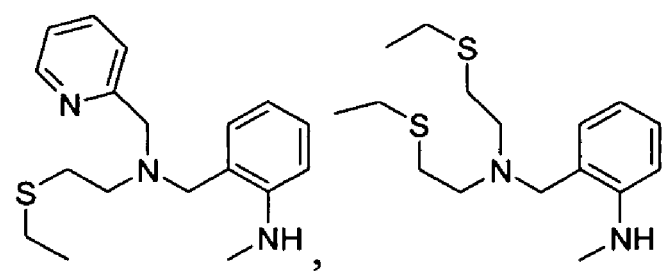
FIG. 7 shows additional exemplary V for the subject naphthofluorescein-based ligands.

Other exemplary ligands may be identified and prepared by the methods taught herein in conjunction with methods known to those of skill in the art. FIG. 6 sets forth a number of non-limiting exemplary moieties that may serve as V in the subject naphthofluorescein-based ligands and compounds.

Various combinations of Lewis bases are possible in V, making reference to the teachings above for V and the knowledge of one skilled in the art. Non-limiting examples include:

(1) V includes 1, 2, 3, or 4 or more Lewis bases in which the atom capable of binding to a metal ion is N, O or some combinations of the two (e.g., one N and one O; two N and one O; two O and one N; etc.). Thus, all possible combinations are contemplated here—1 N, 2 N, 3 N, 4N, 1 O, 2 O, 3 O, 1 S, 2 S, 3 S, 1 N and 1 O, 2 N and 1 O, 1 N and 2 O, 1 N and 1 S, 2 N and 1 S, 2 N and 2 S, 3 N and 1 S ... etc.

(2) V includes Lewis bases that are capable of forming a bidentate, tridentate or tetradentate ligand with a metal ion, optionally involving a Lewis base from the rest of the molecule, such as the O directly attached to the aromatic portion of the naphthofluorescein-based ligand.

(3) V includes 1, 2 or 3 Lewis bases that are N atoms having a particular type, such as an aryl heterocycle, alternatively a pyridine (optionally substituted) etc. All of the ligands called out above may be used, so that a variety of combinations of ligand sets may be achieved.

(4) V includes 1, 2, or 3 Lewis bases that are N atoms and S atoms having a particular type, such as aryl heterocycle, alternatively a pyridine (optionally substituted) for N, and thioether (optionally substituted) for S. All of the ligands called out above may be used, so that a variety of combinations of ligand sets may be achieved.

Further representative examples of the combinations contemplated by the present invention include:

(1) V includes 2 N donors and 1 O donor as Lewis bases that are capable of forming a tridentate ligand with the metal ion;

(2) V includes 1 N donor and 1 O donor as Lewis bases that are capable of forming a bidentate ligand with the metal ion;

(3) V includes 1 N donor and 2 O donors as Lewis bases that are capable of forming a tridentate ligand with the metal ion;

(4) V includes 2 N donors and 1 S donor as Lewis bases that are capable of forming a tridentate ligand with the metal ion;

(5) V includes 1 N donor and 2 S donors as Lewis bases that are capable of forming a tridentate ligand with the metal ion;

(6) All of the forgoing examples may further provide that one or more of the N donors is an aryl heterocycle or some other type of N-donor identified above. For example, the combination described in 1 above could provide further: V includes 2 N donors and 1 O donor as Lewis bases that are capable of forming a tridentate ligand with the metal ion, wherein at least one of the N donors is part of an aryl heterocycle. In a further example, the combination described in 4 above could provide further: V includes 2 N donors and 1 S donor as Lewis bases that are capable of forming a tridentate ligand with the metal ion, wherein at least one of the N donors is part of an aryl heterocycle.

(7) All of the foregoing examples may provide that one or more of the O donors is a carboxylic acid or phenolic group, or some other type of O-donor identified above. For example, the combination described in 3 above could provide further: V includes 1 N donor and 2 O donors as Lewis bases that are capable of forming a tridentate ligand with the metal ion, wherein at least one of the O donors is part of a carboxylic acid;

(8) All of the foregoing examples may optionally be capable of forming a chelate with a metal ion with the O directly attached to the aromatic portion of the naphthofluorescein-based ligand In certain embodiments, the binding affinity of subject ligand to a type of metal ion, target or other analyte will be twice, three times, five, ten, twenty, fifty, hundred or one thousand or more times than the binding affinity of that ligand to another metal ion, target or analyte. In certain embodiments, the change in a fluoroescent property of a subject ligand upon exposure to a type of metal ion, target or other analyte to which it is capable of coordinating will be 25%, 50%, 75%, twice, three times, five, ten, twenty, fifty, hundred or one thousand or more times in the absence of the metal ion, target or other analyte.

In certain embodiments, subject compounds of the present invention contain cleavable moieties. Generally, a cleavable moiety is a chemical moiety that contains a functionality that may be cleaved when using the subject compound under certain conditions. For example, an ester of a subject ligand may be cleavable when exposed to suitable esterases. It is understood that, in certain embodiments, the cleavable moiety should be cleavable under at least some of the conditions during which the subject compound will be used to detect and possible measure the concentration of a metal ion. One example of such a cleavable moiety is the acetate moiety added to ZNP1, MS4, and MS5 as described below, referred to there as ZNP1-Ac, MS4-Ac, and MS5-Ac, respectively.

The inclusion of a cleavable moiety in a subject ligand may give rise to what is commonly known as a prodrug.

In certain instances, the cleavable moiety contains from 1 to 10, 20 30 or 40 carbon atoms. Exemplary functional groups that may be used in a cleavable moiety include ester, amide, amine, and anhydride moieties.

In many instances, the cleavable moiety is chosen so that it may be cleaved during use of the subject compound. In certain embodiments, cleavage of the moiety will "trap" the cleavage products of the subject compound in a location in vivo, such as within a cell or tissue type or one side or the other of the blood-brain barrier. In certain embodiments of the present invention, the choice of the cleavable moiety may be used to affect how quickly a subject compound localizes in one location, for the cleavage rate may be adjusted by modifying the nature, e.g., the type of functional group or length or steric bulk or hindrance or accessibility, of the linker/moiety.

In certain instances, the cleavable moiety may consist of a chemical moiety that is cleaved by an enzyme, such as a naturally occurring enzyme. For example, the moiety may consist of a peptidyl sequence that is cleaved by a peptidase. In certain embodiments, it may be possible to activate a subject compound in a cell or tissue type of interest during in vivo use by using a cleavable moiety that will be cleaved more readily by activity, often enzymatic, that is specific to, or enhanced in, the target cell or tissue type.

The present invention also contemplates the use of photochemical means to cleave a cleavable moiety. To use light to cleave the moiety, it will be necessary to include in the moiety a chemical moiety that is sensitive to light (often at a particular wavelength, e.g., UV). By using light to cleave, it may be possible in certain embodiments to activate a certain subject compound for metal ion detection at a specific time, by controlling when cleavage occurs, and in a specific location, by only exposing the area of a patient of interest to the cleaving light.

Other cleavable moieties that may be used in the present invention are readily identified by those of skill in the art.

Exemplary Scaffold Molecules

In part, this invention is directed to preparation of naphthofluorescein-based ligands. Certain naphthofluorescein-based compounds are useful intermediates in the preparation of such ligands, for they have latent sites of functionality at the ring position indicated below, which are readily diversified to form examples of the subject ligands. One examples of such a scaffold structure is:

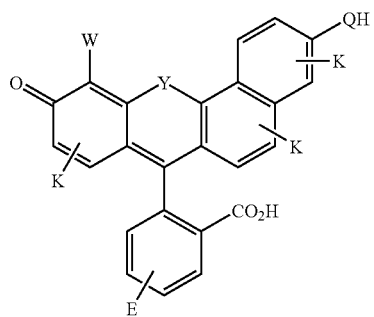

wherein, independently for each occurrence:

Q is O, NR' or S, wherein R' is —H or an alkyl, optionally substituted;

Y is O, S, Se, NR, or C(CH$_3$)$_2$, wherein R is an alkyl and R and the methyl groups of C(CH$_3$)$_2$ are optionally substituted;

W comprises at least one carbon atom bound to the aromatic ring carbon and is a site of latent functionality;

K is optionally one or more of the following substituents of the indicated aromatic ring: aliphatic, alkyl, aralkyl, alkenyl, alkynyl, aryl, amine, acyl, acyloxy, acylamino, amido, alkylthio, carbonyl, alkoxyl, sulfonate, sulfate, sulfamoyl, sulfonyl, sulfoxido, selenoalkyl, nitro, halogen, sulfhydryl, cyano, hydroxyl, carbamoyl, sulfonyl and trifluoromethyl; and E is optionally one or more of the following substituents of the indicated aromatic ring: aliphatic, alkyl, aralkyl, alkenyl, alkynyl, aryl, amine, acyl, acyloxy, acylamino, amido, alkylthio, carbonyl, alkoxyl, sulfonate, sulfate, sulfamoyl, sulfonyl, sulfoxido, selenoalkyl, nitro, halogen, sulfhydryl, cyano, hydroxyl, carbamoyl, sulfonyl and trifluoromethyl.

The term "latent functionality" when used in connection with W is art-recognized and includes all W for which it is possible to prepare by synthetic methods a moiety from W having at least one, and possibly more, Lewis base(s) which may, under appropriate conditions, coordinate one or more metal ions, targets or other analytes of interest.

In the above Formula, W includes a carbon atom bound directly to the aromatic ring structure and any additional atoms as required to provide a site having latent functionality. Examples of W include —CH$_2$X, —C(O)H, —C(O)OR2, —C(O)OH, —C(O)X, —CN wherein X is halogen, hydroxyl, amine, thiol and the like, and R2 is an aliphatic, alkyl, aralkyl, alkenyl, alkynyls, aryl or heterocyclyl, and alternatively, all of the foregoing with a methylene adjacent to the aromatic ring, optionally substituted.

Examples of subject scaffold structures include:

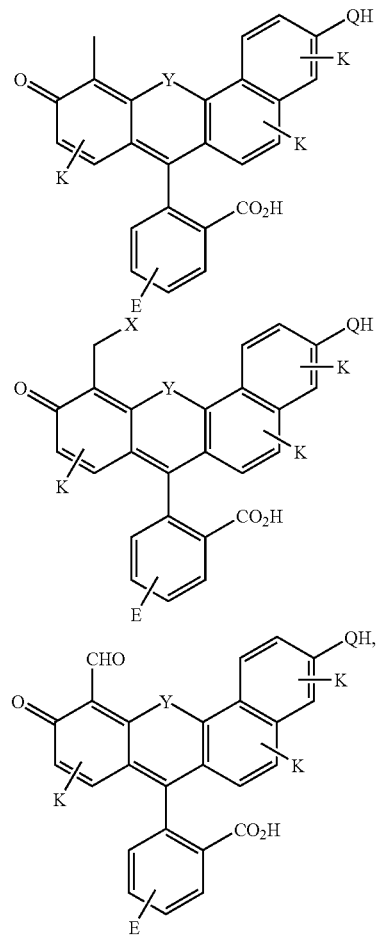

wherein X is halogen.

The subject scaffold compounds may be reacted further in one or more steps to provide the subject ligands. One of ordinary skill in the art will appreciate that the reagents chosen for reaction at the latent functionality W will only be limited by the reactivity of that reagent with that particular functionality, with the ultimate goal being preparing the subject naphthofluorescein-based compounds and ligands.

The subject scaffold compounds may have uses in addition to being intermediates to naphthofluorescein-based compounds and ligands.

Exemplary Metal Ions

The metal atom that may form a coordination complex with a subject ligand or used in the subject methods may be selected from those that have usually at least three, four, five, six, seven coordination sites or more. In certain embodiments, the subject ligands and methods may be used to coordinate a wide range of metal ions, including light metals (Groups IA and IIA of the Periodic Table), transition metals (Groups IB-VIIIB of the Periodic Table), posttransition metals, metals of the lanthanide series and metals of the actinide series. A non-limiting list of metal ions for which the present invention may be employed (including exemplary oxidation states for them) includes: $Li^+$, $Na^+$, $K^+$, $Mg^+$, $Ca^+$, $Zn^{2+}$, $Cd^{2+}$, $Hg^{2+}$, $Cu^{2+}$, $Pd^{2+}$, $Pt^{2+}$.

The design of a subject compound for detecting a particular metal ion will be possible by one of skill in the art, wherein issues such as selectivity, quantum yield, ease of synthesis and the like will be important criteria.

Exemplary Methods

In part, the subject invention is directed to a method of detecting, and optionally quantifying the concentration of, a metal ion in a sample, comprising: a) adding to a sample the naphthofluorescein-based ligands of the subject invention; b) measuring the fluorescence of said ligand in said sample; and c) determining whether a metal ion is present in said sample, and optionally the concentration of said metal ion in said sample.

In a further embodiment, said sample is a cell. In a further embodiment, said sample is in vivo. In a further embodiment, the method further comprises measuring the fluorescence of said ligand in said sample at a different concentration of said ligand. In a further embodiment, said metal ion is a transition metal ion. In a further embodiment, said metal ion is $Zn^{2+}$. In a further embodiment, said metal ion is $Hg^{2+}$.

In part, the subject invention is directed to a method of detecting, and optionally quantifying the concentration of, a target in a sample, comprising: a) mixing with a sample the naphthofluorescein-based compound of the subject invention; b) measuring the fluorescence of said compound in said sample; and c) determining whether the target is present in said sample, and optionally the concentration of said target in said sample.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

In part, the subject invention is directed to a diagnostic kit for a metal ion, comprising: a) the naphthofluorescein-based ligand of the subject invention; and b) instructions for using said ligand to detect a metal ion in a sample.

In a further embodiment, the diagnostic kit further comprises identifying a patient in need of determining the presence of a metal ion in a biological sample of said patient. In a further embodiment, said instructions provide for said sample to be in vivo.

In part, the subject invention is directed to a diagnostic kit for a target, comprising: a) the naphthofluorescein-based compound of the subject invention; and b) instructions for using said compound to detect a target in a sample.

Fluorescence Assays

Instrumentation

Fluorescence of a ligand provided by the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon or Molecular Dynamics. In certain embodiments, the device is coupled to a signal amplifier and a computer for data processing.

General Aspects

In general, assays using naphthofluorescein-based ligands provided by the present invention involve contacting a sample with such a ligand and measuring fluorescence. The presence of a metal ion that interacts with the ligand may alter fluorescence of the ligand in many different ways. Essentially any change in fluorescence caused by the metal may be used to determine the presence of the metal and, optionally the concentration of the metal, in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the ligand to fluoresce. To determine the excitation spectrum for a ligand in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by metal in a sample may be used as the basis for determining the presence, and optionally, the concentration of metal in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a metal in a sample may be used to determine the presence or concentration of the metal ion in the sample. Changes in excitation or emission spectra may be measured as ratios of two wavelengths. A range of changes are possible, from about a few nms to 5, 10, 15, 25, 50, 75 100 or more nms.

Quantum yield, Φ, may be obtained by comparison of the integrated area of the corrected emission spectrum of the sample with that of a reference solution. A preferred reference solution is a solution of fluorescein in 0.1 N NaOH, quantum efficiency 0.95. The concentration of the reference is adjusted to match the absorbance, Abs, of the test sample. The quantum yields may be calculated using the following equation:

$$\Phi_{sample} = \Phi_{standard} \times \frac{\int emission_{sample}}{\int emission_{standard}} \times \frac{Abs_{standard}}{Abs_{sample}}$$

A change in quantum yield caused by a metal ion may be used as the basis for detecting the presence of the metal in a sample and may optionally be used to determine the concentration of the metal ion. A range of changes are possible in the subject invention. For example, the difference in the quantum yield for a subject naphthofluorescein-based ligand in the presence of a metal ion may be about 10%, 25%, 50%, 75% of the quantum yield of the subject naphthofluorescein-based ligand in the absence of the metal, or it may be 2, 3, 5, 10, 100, 200, 1000, 10000 times greater or more. The same values may be used to describe changes observed in intensity in such the subject assays.

It is expected that some samples will contain compounds that compete for metal-binding with the fluorescent ligand. In such cases, the fluorescence measurement will reflect this competition. In one variation, the fluorescence may be used to determine the presence or concentration of one or more such metal binding compounds in a sample.

In vitro Assays

In one variation, the presence of a metal ion in a sample is detected by contacting the sample with a naphthofluorescein-based ligand that is sensitive to the presence of the metal. The fluorescence of the solution is then determined using one of the above-described devices, preferably a spectrofluorimeter. Optionally, the fluorescence of the solution may be compared against a set of standard solutions containing known quantities of the metal. Comparison to standards may be used to calculate the concentration of the analyte, i.e. the metal ion.

The metal may be essentially any substance described above. The concentration of the metal may change over time and the fluorescent signal may serve to monitor those changes. For example, the particular form of the metal that interacts with the ligand may be produced or consumed by a reaction occurring in the solution, in which case the fluorescence signal may be used to monitor reaction kinetics.

In certain embodiments, the sample is a biological fluid, lysate, homogenate or extract. The sample may also be an environmental sample such as a water sample, soil sample, soil leachate or sediment sample. The sample may be a biochemical reaction mixture containing at least one protein capable of binding to or altering a metal. Samples may have a pH of about 5, 6, 7, 8, 9, 10, 11, 12 or higher.

In vivo Assays

In another variation, the presence of a metal ion in a biological sample may be determined using a fluorescence microscope and the subject naphthofluorescein-based ligands. The biological sample is contacted with the fluorescent sensor and fluorescence is visualized using appropriate magnification, excitation wavelengths and emission wavelengths. In order to observe co-localization of multiple analytes, the sample may be contacted with multiple fluorescent molecules simultaneously. In certain embodiments the multiple fluorescent molecules differ in their emission and/or excitation wavelengths.

Biological samples may include bacterial or eukaryotic cells, tissue samples, lysates, or fluids from a living organism. In certain embodiments, the eukaryotic cells are nerve cells, particularly glutamate neurons. In other embodiments, the eukaryotic cells are neurons with mossy fiber terminals isolated from the hippocampus. Tissue samples are preferably sections of the peripheral or central nervous systems, and in particular, sections of the hippocampus containing mossy fiber terminals. It is also anticipated that the detection of a metal in a cell may include detection of the metal in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices.

Assays using Subject Compounds

The solution or biological sample is contacted with a subject ligand, and fluorescence of the ligand is excited by light with wavelengths ranging from 340 nm to 600 nm. Light emitted by the ligand is detected by detecting light of wavelengths greater than 480 nm. In certain embodiments the excitation wavelengths range from 450 to 510 nm and the detection wavelengths are greater than 535 nm.

Results

Figure 8:
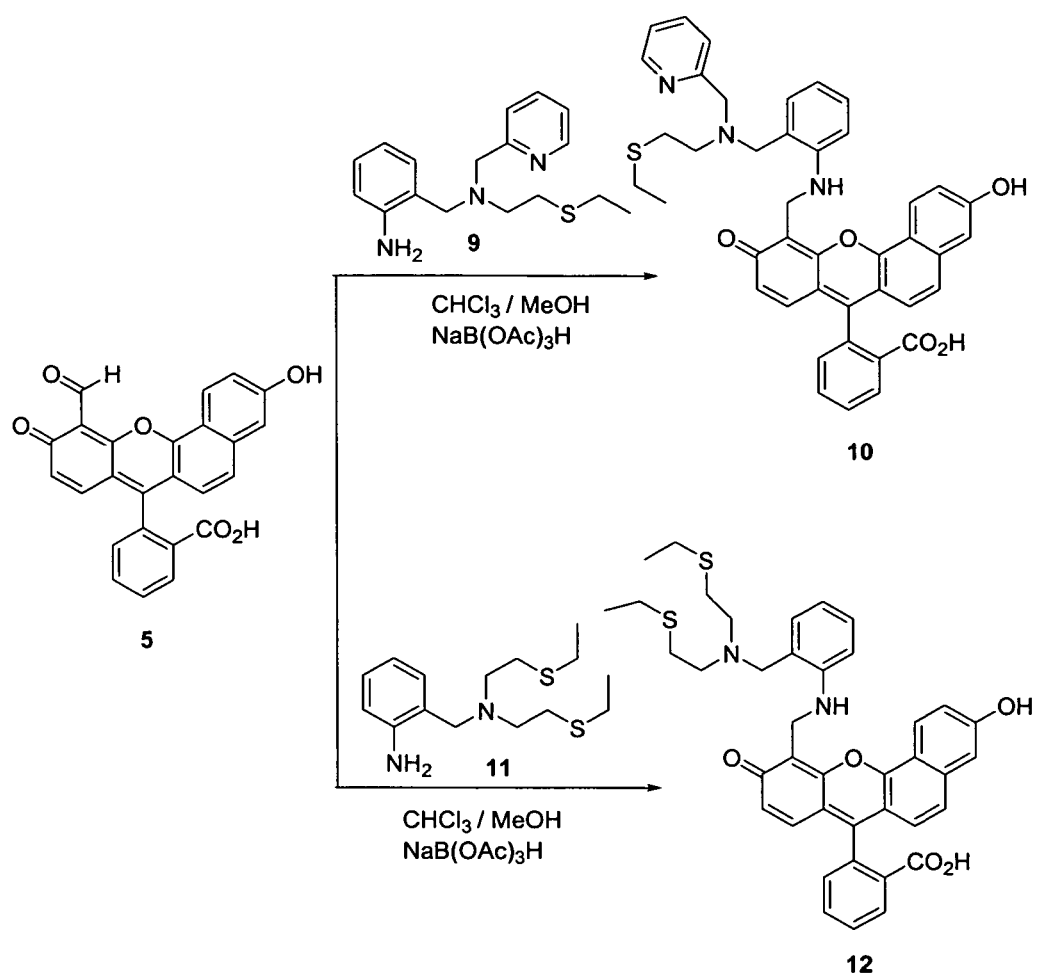
FIG. 8 depicts the synthesis of MS4 and MS5.
Figure 9:
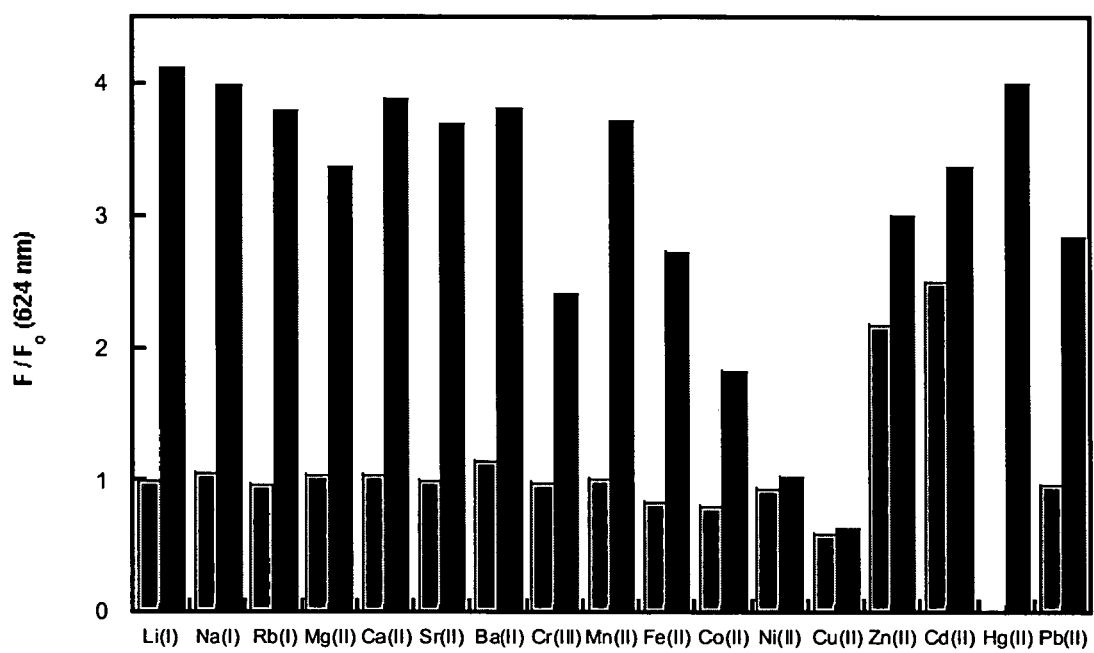
FIG. 9 depicts the ratiometric fluorescence spectroscopic responses of MS4 to various metal ions. Bars represent the ratio of fluorescence intensities collected at 624 and 528 nm ($F_{624}/F_{528}$). All spectra were acquired in 50 mM HEPES, 100 mM KCl, pH 8. Grey bars represent the addition of an excess of the appropriate metal ion (50 equiv metal ion of interest) to a 5 µM solution of MS4. Dark grey bars represent the subsequent addition of 50 equiv $Hg^{2+}$ to the solution. Excitation was provided at 499 nm.
Figure 10:
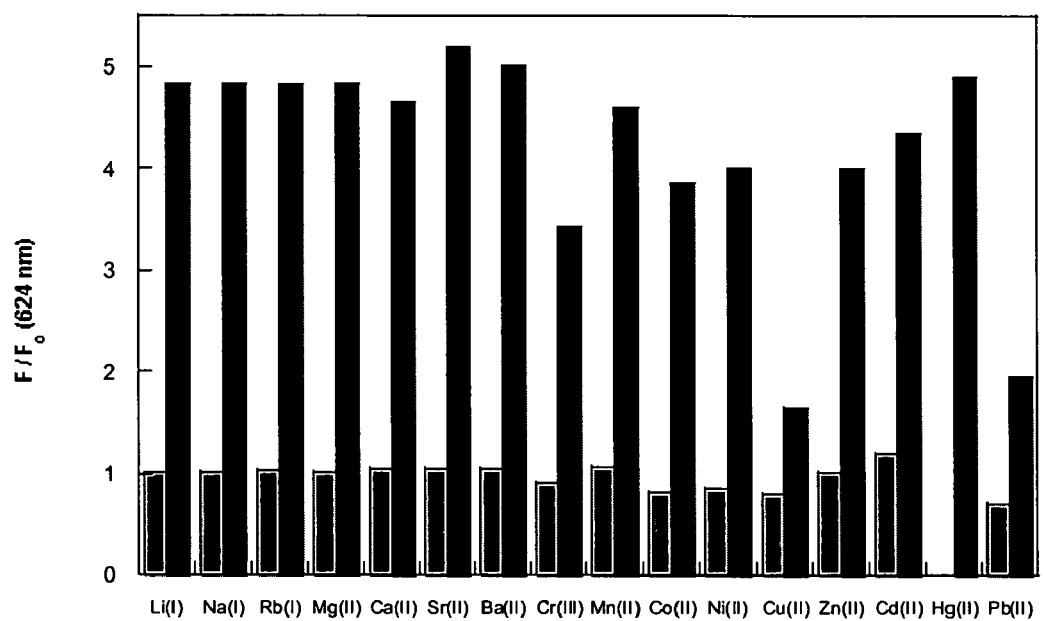
FIG. 10 depicts the ratiometric fluorescence spectroscopic responses of MS5 to various metal ions. Bars represent the ratio of fluorescence intensities collected at 624 and 528 nm ($F_{624}/F_{528}$). All spectra were acquired in 50 mM HEPES, 100 mM KCl, pH 8. Grey bars represent the addition of an excess of the appropriate metal ion (50 equiv metal ion of interest) to a 5 µM solution of MS5. Dark grey bars represent the subsequent addition of 50 equiv $Hg^{2+}$ to the solution. Excitation was provided at 499 nm.

The preparation of exemplary subject naphthofluorescein-based ligandd is shown in FIGS. 1 and 8. This convergent approach offers a general method for assembling asymmetric semi-naphthofluorescein dyes as well as a useful monofunctionalized aldehyde scaffold (among others) for attachment to a wide variety of metal ion receptors. In this synthetic scheme, reaction of 2-methylresorcinol with phthalic anhydride in the presence of $AlCl_3$ generates 2'-carboxy-3-methyl-2,4-dihydroxybenzophenone 1 in 78% yield after recrystallization from methanol/water mixtures. Condensation of benzophenone 1 and 1,6-dihydroxynaphthalene in methanesulfonic acid furnishes the desired asymmetric semi-naphthofluorescein dye 2 in excellent yield (79%) after column chromatography. Notably, analysis of the crude reaction mixture shows that only trace amounts of symmetric fluorescein and naphthofluorescein side products are formed (<5% each). The installation of benzoate protecting groups proceeds smoothy to afford 3 in 83% yield after column chromatography. Bromination of 3 under mild free radical conditions produces 4 in 78% yield. Product 4 was carried on without purification to the next step. Oxidation and benzoate deprotection are achieved in a one-pot reaction by treatment of bromide 4 with dimethyl sulfoxide and sodium bicarbonate under anhydrous conditions. The resulting aldehyde product 5 is obtained in modest yield (37%) after column chromatography. The pre-assembled semi-naphthofluorescein aldehyde is a convenient synthon for the preparation of the subject naphthofluorescein-based compounds. Schiff-base condensation of 5 and aniline 6 followed by reduction of the imine intermediate with sodium triacetoxyborohydride delivers ZNP1 in 55% yield.

Figure 3:
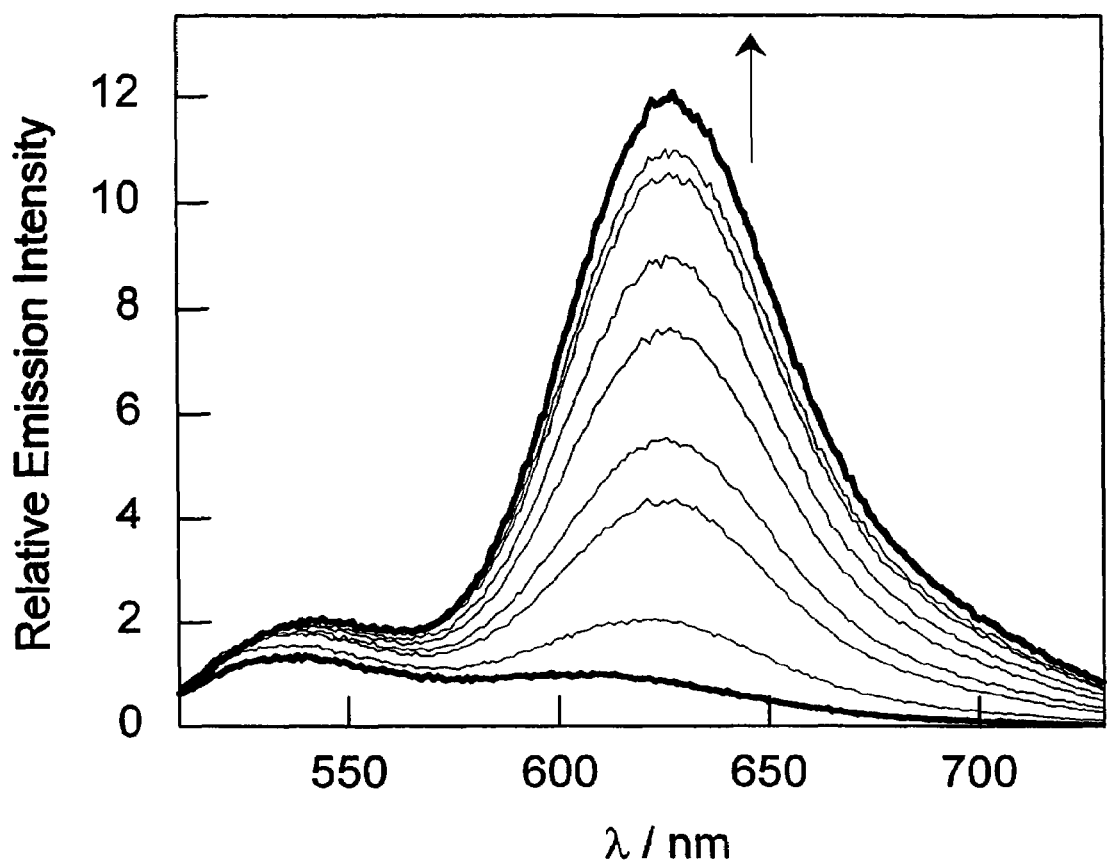
FIG. 3. Ratiometric fluorescence spectroscopic response of 20 µM ZNP1 to buffered $Zn^{2+}$ solutions. Spectra were acquired in 50 mM HEPES, 100 mM KCl, pH 7.5. Excitation was provided at 499 nm. A standard EDTA/$Ca^{2+}$/$Zn^{2+}$ dual-metal buffer system was employed to deliver controlled concentrations of buffered free $Zn^{2+}$. The spectra shown are for free $Zn^{2+}$ buffered at 0, 0.17, 0.42, 0.79, 1.3, 2.1, 3.4, 5.6, and 10.2 nM, respectively. The fluorescence responses occur immediately upon mixing.

ZNP1 was evaluated at physiological ionic strength and pH [50 mM HEPES (4-(2-hydroxyethyl)-1-piperazineethanesulfonic acid), 100 mM KCl, pH 7.5] in the presence of EDTA (ethylenediaminetetraacetic acid) to scavenge adventitious metal ions. The semi-naphthofluorescein probe exhibits two absorption bands in the visible region centered at 503 nm ($\epsilon=7.2\times10^3$ $M^{-1}cm^{-1}$) and 539 nm ($\epsilon=6.7\times10^3$ $M^{-1}cm^{-1}$). Upon excitation at 499 nm, two attendant emission bands of comparable intensity are observed with maxima at 528 nm and 604 nm (FIG. 3). The quantum yield for apo ZNP1 is 0.02. The absorption and emission profiles of ZNP1 suggests, as hypohesized above, that the apo chemosensor has electronic contributions from both naphthoxyquinone and phenoxynaphthoquinone tautomeric forms.

The observed changes in absorption and emission spectra occur up to a 1:1 [$Zn^{2+}$][ZNP1] ratio, indicating the likely formation of a 1:1 complex. Upon addition of $Zn^{2+}$, the visible absorption profile of the ZNP1 chemosensor red shifts to a single broad peak centered at 547 nm ($\epsilon=2.2\times10^4$ $M^{-1}$ $cm^{-1}$). Excitation at 499 nm produces a fluorescence spectrum featuring one dominant emission band centered at 624 nm with a minor component centered at 545 nm (FIG. 3). The quantum yield for $Zn^{2+}$-ZNP1 complex is 0.05. Taken together, these data suggest that $Zn^{2+}$-bound ZNP1 resides primarily in the phenoxynaphthoquinone tautomer, and that ZNP1 provides an effective platform for single excitation, dual emission ratiometric sensing of $Zn^{2+}$ through controllable $Zn^{2+}$-induced switching between the fluorescein- and naphthofluorescein-like tautomers. The ratio of naphthofluorescein- to fluorescein-like emission intensities ($\lambda_{624}/\lambda_{528}$) upon 499-nm excitation varies from 0.4 in the absence of $Zn^{2+}$ to 7.1 in the presence of $Zn^{2+}$, an 18-fold increase.

Figure 4:
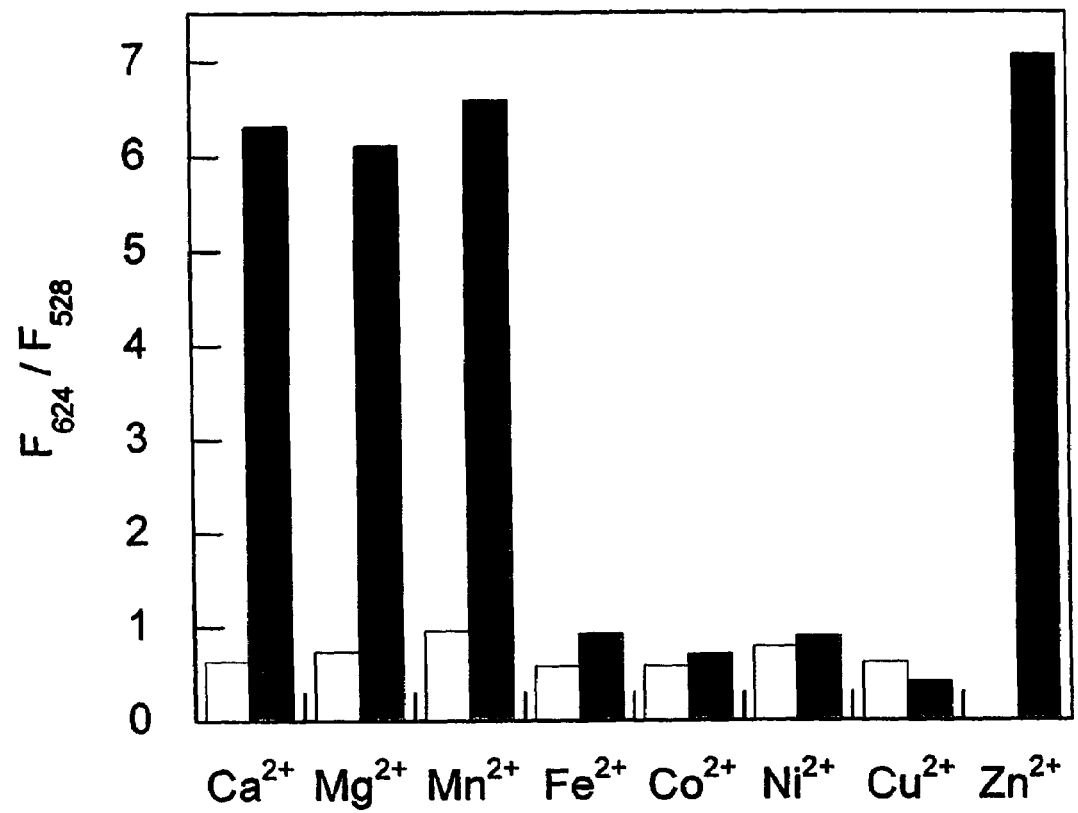
FIG. 4. Ratiometric fluorescence spectroscopic responses of ZNP1 to various metal ions. Bars represent the ratio of fluorescence intensities collected at 624 and 528 nm ($F_{624}/F_{528}$). All spectra were acquired in 50 mM HEPES, 100 mM KCl, pH 7.5. White bars represent the addition of an excess of the appropriate metal ion (2 mM for $Ca^{2+}$ and $Mg^{2+}$, 100 µM for all other metal ions) to a 10 µM solution of ZNP1. Grey bars represent the subsequent addition of 100 µM $Zn^{2+}$ to the solution. Excitation was provided at 499 nm.

FIG. 4 displays the fluorescence response of a 10 μM solution of ZNP1 in the presence of various divalent metal ions. The emission profiles of apo or $Zn^{2+}$-bound ZNP1 are unperturbed in the presence of 2 mM $Ca^{2+}$ or $Mg^{2+}$, indicating a degree of selectivity for $Zn^{2+}$ over these biologically competing alkaline earth cations. Other first-row transition metal ions including $Cu^{2+}$, $Ni^{2+}$, $Co^{2+}$, $Fe^{2+}$, and $Mn^{2+}$ at 10-fold excess over probe produce no discernable change in emission ratios. Of these transition-metal ions, only the sample containing $Mn^{2+}$ affords a ratiometric fluorescence response upon the subsequent addition of 100 μM $Zn^{2+}$.

The binding affinity of ZNP1 for $Zn^{2+}$ was characterized by using a dual-metal single-ligand buffer system. Varying the total $Zn^{2+}$ concentrations between 0 and 1 mM in the presence of constant concentrations of $Ca^{2+}$ (2 mM) and EDTA (1 mM) delivers controlled concentrations of buffered free $Zn^{2+}$ between 0 and 25 nM. ZNP1 responds to nanomolar concentrations of free ionic $Zn^{2+}$, and binding of $Zn^{2+}$ to the probe was monitored by measuring the ratio of fluorescence intensities collected at 624 and 528 nm. This analysis was performed in triplicate using different preparations of $Ca^{2+}$/$Zn^{2+}$/EDTA buffers to determine an apparent $K_d$ value of 0.55±0.1 nM for the fluorescence-responsive 1:1 $Zn^{2+}$-ZNP1 complex.

Figure 5:
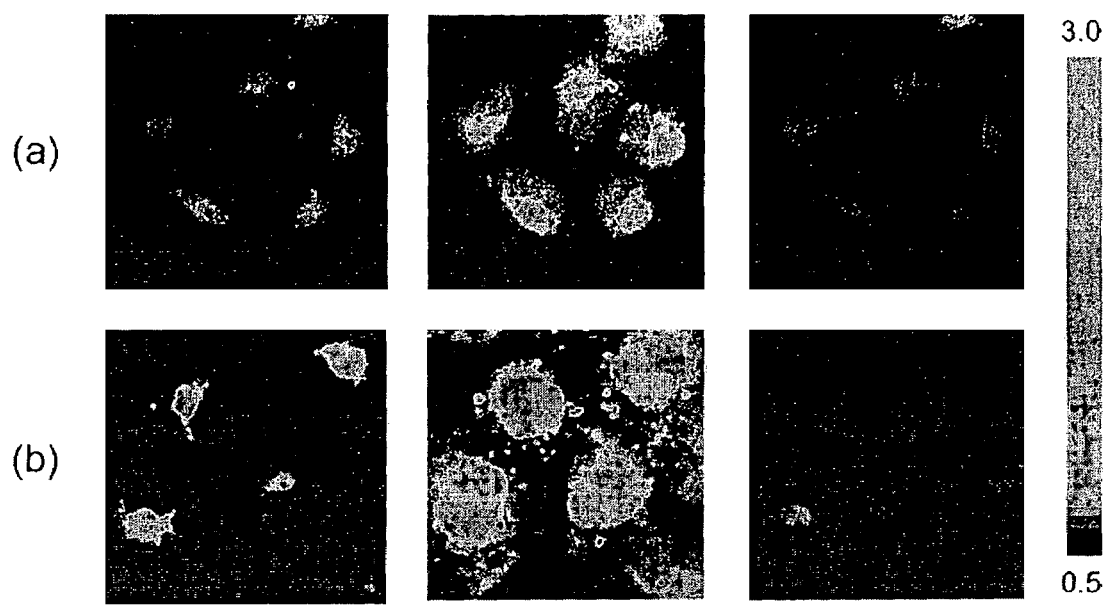
FIG. 5. Ratio confocal fluorescence imaging in COS-7 cells using the Zeiss LSM510 META system operating in the lambda mode. Fluorescence was collected in 10.7 nm optical windows centered at 612 and 526 nm. Pseudocolor figures depict the ratio of fluorescence intensities at these two emission wavelengths. (a) Ratio confocal fluorescence images of live COS-7 cells labeled with ZNP1. Incubation of cells with 20 µM ZNP1-Ac for 20 min at 37° C. (left), ZNP1-stained cells loaded with 50 µM Zn(pyrithione)$_2$ for 5 min (middle), and reversal of the cytosolic ratio enhancements with 100 µM TPEN (right). Confocal images were taken from a middle optical section (vertical dimension) of the cell samples. (b) Confocal fluorescence images of NO-triggered release of endogenous $Zn^{2+}$ in live COS-7 cells. Incubation of cells with 20 µM ZNP1-Ac for 20 min at 37° C. (left), ZNP1-stained cells treated with 10 mM SNOC (S-nitrosocysteine, middle) for 1 hr, and reversal of the observed ratio increases with 2 mM TPEN (right). Confocal images were taken from a middle optical section (vertical dimension) of the cell samples.

Initial experiments established that ZNP1 is impermeable to cell membranes. We therefore prepared the non-fluorescent diacetate derivative of ZNP1, ZNP1-Ac, anticipating that this more lipophilic derivative would permeate the cell and be transformed to fluorescent ZNP1 by the action of intracellular esterases. Incubation of COS-7 cells with 20 μM ZNP1-Ac for 20 min at 37° C. results in intracellular staining by ZNP1 as determined from scanning confocal fluorescence microscopy measurements on live samples. Ratiometric fluorescence imaging of ZNP1-stained cells is readily performed by using the META detection system operating in lambda mode with optical windows centered at 612 and 526 nm. The ratio of fluorescence intensities at 612 and 526 nm for ZNP1-loaded COS-7 cells reveals that these mammalian cells contain low levels of available ionic $Zn^{2+}$ (FIG. 5a). Prompt increases in the ratio of cytosolic fluorescence intensities collected at 612 and 526 nm are observed upon the addition of exogenous $Zn^{2+}$ (50 μM) carried by the ionophore pyrithione (2-mercaptopyridine N-oxide, FIG. 5a). Treatment of the cells with the membrane-permeable metal ion chelator TPEN [N,N,N',N'-tetra(2-picolyl)ethylenediamine, 100 μM] reverses the fluorescent ratio enhancements to baseline levels (FIG. 5a). These experiments indicate that ZNP1 can monitor changes in intracellular [$Zn^{2+}$] reversibly.

The successful use of ZNP1 for monitoring changes in intracellular $Zn^{2+}$ concentrations using ratiometric fluorescence imaging led us to apply this probe for detecting endogenous pools of intracellular $Zn^{2+}$. To achieve this goal we took advantage of the role of nitric oxide (NO), a key contributor to intracellular $Zn^{2+}$ homeostasis. NO is an important and versatile signaling molecule with far-ranging physiological and pathological functions. Relevant cellular targets of NO include transition metal ions, and cysteine thiol residues at structural and/or catalytic sites of proteins react with NO to form S-nitrosothiols. In the case of zinc-dependent metalloproteins, formation of S-nitrosocysteine adducts labilizes $Zn^{2+}$ from the polypeptide scaffold. In particular, NO induces $Zn^{2+}$ release from metallothionein and inhibits the DNA-binding activity of the dizinc(II)-dependent transcription factor LAC9. To test whether ZNP1 can detect the intracellular release of $Zn^{2+}$ triggered by NO, we treated ZNP1-stained COS-7 cells (FIG. 5b) with the endogenous NO donor S-nitrosocysteine (10 mM). Ratiometric fluorescence imaging using the META detection system operating in lambda mode establishes a rise in intracellular [$Zn^{2+}$] through an increase in the ratios of fluorescence intensity collected at 612 and 526 nm (FIG. 5b). The observed ratio enhancements are reversed by TPEN treatment (2 mM, FIG. 5b), indicating that the NO-induced signals are attributable to labilized ionic $Zn^{2+}$, as observed previously.

Exemplifcation

The present invention now being generally described, it may be more readily understood from the following examples, which are presented herein for illustration only and should not be construed as limiting the invention.

Synthetic Materials and Methods. Silica gel 60 (70-230 mesh, Merck) and octadecyl-functionalized silica gel (RP18, Aldrich) were used for column chromatography. Analytical thin layer chromatography was performed by using Merck 60 F254 silica gel and Merck RP-18 F254S silica gel (precoated sheets, 0.25 mm thick). Solvents for synthesis were of reagent grade or better and were dried according to standard methods. 2-[Bis(2-pyridylmethyl)-aminomethyl]aniline (6) was prepared as described previously (Burdette, S. C., Frederickson, C. J., Bu, W. & Lippard, S. J. (2003) J. Am. Chem. Soc. 125, 1778-1787). All other reagents for synthesis were purchased and used as received. $^1$H NMR spectra were collected in $CDCl_3$, $CD_3OD$, or $d_7$-dimethylformamide (Cambridge Isotope Laboratories) at 25° C. at the MIT Department of Chemistry Instrumentation Facility (DCIF) on either a Varian Inova 500 or a Varian Mercury 300 spectrometer. All chemical shifts are reported in the standard notation of parts-per-million; positive chemical shifts are to higher frequency from the given reference. High-resolution mass spectral analyses were carried out at the MIT DCIF. Formula numbers below are used in reference to FIGS. 1 and 8. The aniline derivatized ligands 9 and 11 were synthesized according to previously published procedures. Chang, C. J.; Jaworski, J.; Nolan, E.

M.; Sheng, M.; Lippard, S. J. *Prod. Nat. Acad. Sci. USA* 2004, 101, 1129-1134; Nolan, E. M.; Lippard, S. J. *Inorg. Chem.* 2004, 43, 8310-8317; Nolan, E. M.; Lippard, S. J. *J. Am. Chem. Soc.* 2003, 125, 14270-14271.

Anhydrous methanol, chloroform and dichloromethane were purchased from Aldrich and used as received. Sodium triacetoxyborohydride was also purchased from Aldrich and used as received.

Analytical thin-layer chromatography (TLC) was performed by using Merck F254 silica gel 60 plates (0.25 mm thickness) and TLC plates were viewed with UV light. Whatman silica gel-60 plates (1 mm thickness) were used as the solid phase for preparative TLC. NMR spectra were collected by using a Varian 300 MHz spectrophotometer operating at 283 K and the spectra were referenced to internal standards.

Cell Culture. COS-7 cells were cultured in Dulbecco's Modified Eagle Medium (DMEM, Invitrogen) supplemented with 10% fetal calf serum (FCS, Invitrogen), glutamine (2 mM), and gentamycin (50 ug/ml, Invitrogen). One day before imaging, cells were passed and plated on 24 mm glass coverslips coated with poly-L-lysine (50 ug/ml) and moved to glass-bottomed live imaging dishes (MatTek Corporation, Ashland, Mass.). Immediately prior to labeling, cells were washed twice with DMEM, and then the medium was replaced with $Zn^{2+}$-free Krebs ringer buffer. Krebs ringer buffer was prepared according to a published method. Cells were incubated with ZNP1 (20 µM) for 20 min at 37° C. under 5% $CO_2$, and then washed once with Krebs media before imaging.

EXAMPLE 1

2'-Carboxy-3-methyl-2,4-dihydroxybenzophenone (1). Under an argon atmosphere, 2-methylresorcinol (10.0 g, 80.6 mmol) and phthalic anhydride (11.2 g, 75.6 mmol) were combined in dry nitrobenzene (250 mL). The mixture was cooled to 0° C. and aluminum(III) chloride (23.5 g, 176 mmol) was added in one portion. The resulting dark olive slurry was allowed to warm to room temperature and stirred for an additional 16 h under argon. The reaction was poured into a vigorously stirring mixture of hexanes (300 mL) and 1 M HCl (1 L). The precipitate was filtered and recrystallized twice from methanol/water to afford benzophenone 1 as a beige powder (16.0 g, 78% yield). $^1$H NMR ($CD_3OD$, 500 MHz): δ 8.05 (1 H, dd, $J_1$=8.0 Hz, $J_2$=1.0 Hz), 7.62 (2 H, dt, $J_1$=33.0 Hz, $J_2$=9.0 Hz), 7.33 (1 H, d, J=7.5 Hz), 6.74 (1 H, d, J=8.5 Hz), 6.20 (1 H, d, J=8.5 Hz), 2.05 (3 H, s). HRMS (ESI) calcd for [M–H]$^-$ 271.0601, found 271.0601.

EXAMPLE 2

4-Methyl-3,10-dihydroxy-spiro[7H-benzo[c]xanthen-7,1'(3'H)-isobenzofuran]-3'-one (2)

2'-Carboxy-3-methyl-2,4-dihydroxybenzophenone (1, 8.16 g, 30.0 mmol) and 1,6-dihydroxynaphthalene (4.81 g, 30.0 mmol) were combined in methanesulfonic acid (120 mL) and sealed in a thick-walled glass tube. The resulting viscous mixture was stirred at 90° C. for 24 h. The reaction was poured into ice-cold water (1 L) and the precipitate was filtered and washed with water (3×200 mL). Purification by flash column chromatography (silica gel, 9:1 dichloromethane/methanol) furnished semi-naphthofluorescein 2 as a brick red powder (9.40 g, 79% yield). $^1$H NMR ($CD_3OD$, 500 MHz): δ 8.41 (1 H, d, J=9.0 Hz), 8.00 (1 H, d, J=7.0 Hz), 7.69 (2 H, m), 7.27 (1 H, dd, $J_1$=8.5 Hz, $J_2$=3.5 Hz), 7.23 (1 H, d, J=10.0 Hz), 7.16 (1 H, d, J=7.5 Hz), 7.09 (1 H, br s), 6.59 (2 H, m), 6.46 (1 H, d, J=8.5 Hz), 2.48 (3 H, s). HRMS (ESI) calcd for [M+H]$^+$ 397.1071, found 397.1057.

EXAMPLE 3

4-Methyl-3,10-dibenzoate-spiro[7H-benzo[c]xanthen-7,1'(3'H)-isobenzofuran]-3'-one (3)

Under an argon atmosphere, 4-methyl-3,10-dihydroxy-spiro[7H-benzo[c]xanthen-7,1'(3'H)-isobenzofuran]-3'-one (2, 396 mg, 1.00 mmol) and benzoic anhydride (475 mg, 2.10 mmol) were combined in dry pyridine (10 mL). The resulting dark red mixture was refluxed under argon for 3 h at 140° C., cooled to 75° C., and poured into vigorously stirring cold water (25 mL). The peach colored precipitate was filtered and washed with water (2×100 mL). Purification by flash column chromatography (silica gel, 2:1 hexanes/ethyl acetate) delivered dibenzoate 3 as a lemon yellow solid (500 mg, 83% yield). $^1$H NMR ($CDCl_3$, 500 MHz): δ 8.64 (1 H, d, J=9.0 Hz), 8.27 (4 H, m), 8.09 (1 H, d, J=7.5 Hz), 7.68 (5 H, m), 7.57 (5 H, m), 7.50 (1 H, d, J=9.0 Hz), 7.21 (1 H, d, J=7.5 Hz), 6.97 (1 H, d, J=8.5 Hz), 6.86 (1 H, d, J=8.5 Hz), 6.82 (1 H, d, J=8.5 Hz), 2.58 (s, 3H). HRMS (ESI) calcd for [M+H]$^+$ 605.1595, found 605.1611.

EXAMPLE 4

4-Bromomethyl-3,10-dibenzoate-spiro[7H-benzo[c]xanthen-7,1'(3'H)-isobenzofuran]-3'-one (4)

4-Methyl-3,10-dibenzoate-spiro[7H-benzo[c]xanthen-7,1'(3'H)-isobenzofuran]-3'-one (3, 4.85 g, 8.02 mmol) and 1,3-dibromo-5,5-dimethylhydantoin (2.58 g, 9.02 mmol) were combined in dry chlorobenzene (175 mL). Acetic acid (100 uL) and 1,1'-azobis(cyclohexanecarbonitrile) (VAZO 88, 108 mg, 0.44 mmol) were added and the solution was stirred at 50° C. for 96 h. Hot water (200 mL) was added to the reaction and the organic layer was separated, washed with water (2×100 mL), and dried over $Na_2SO_4$. The solvent was removed by rotary evaporation and the remaining oil was dissolved in toluene (10 mL). Precipitation with ethanol (75 mL) gives bromomethyl compound 4 as a pale peach powder (4.30 g, 78% yield) that was used without further purification. $^1$H NMR ($CDCl_3$, 500 MHz): δ 8.75 (1 H, d, J=9.5 Hz), 8.72 (1 H, d, J=9.5 Hz), 8.30 (4 H, m), 8.27 (1 H, m), 7.73 (5 H, m), 7.60 (5 H, m), 7.24 (1 H, m), 7.10 (1 H, m), 6.96 (1 H, t, J=9.5 Hz), 6.86 (1 H, d, J=9.0 Hz), 4.94 (2 H, m). HRMS (ESI) calcd for [M+H]$^+$ 683.0700, found 683.0692.

EXAMPLE 5

4-Carboxaldehyde-3,10-dibenzoate-spiro[7H-benzo[c]xanthen-7,1'(3'H)-isobenzofuran]-3'-one (5)

4-Bromomethyl-3,10-dibenzoate-spiro[7H-benzo[c]xanthen-7,1'(3'H)-isobenzofuran]-3'-one (4, 200 mg, 0.29 mmol) and sodium bicarbonate (200 mg, 2.38 mmol) were combined in dry dimethyl sulfoxide (7 mL) and the mixture was heated under argon for 3 h at 140° C. The reaction was cooled to 80° C. and poured into 4 N HCl (35 mL). The resulting precipitate was filtered and washed with water (50 mL). Purification by flash column chromatography (silica gel, 19:1 dichloromethane/methanol) yields aldehyde 5 as a red solid (45 mg, 37% yield). $^1$H NMR (25:1 $CDCl_3/CD_3OD$, 500 MHz): δ 10.84 (1 H, s), 8.81 (2 H, m), 8.45 (1 H, t, J=7.5 Hz), 8.25 (1 H, d, J=9.0 Hz), 8.02 (1 H, m), 7.96 (1 H, m), 7.65 (2 H, m), 7.46 (1 H, m), 7.10 (1 H, d, J=7.5 Hz), 6.88 (1 H, d, J=9.0 Hz), 6.63 (1 H, d, J=7.0 Hz). HRMS (ESI) calcd for [M+H]$^+$ 411.0863, found 411.0876.

EXAMPLE 6

4-[12-{Bis(2-pyridylmethyl)aminomethyl}-N-methylaniline]-3,10-dibenzoate-spiro[7H-benzo[c]xanthen-7,1'(3'H)-isobenzofuran]-3'-one (Zin-naphthopyr 1, ZNP1, 7)

4-Carboxaldehyde-3,10-dibenzoate-spiro[7H-benzo[c]xanthen-7,1'(3'H)-isobenzofuran]-3'-one (5, 52 mg, 0.127 mmol) and 2-[bis(2-pyridylmethyl)-aminomethyl]aniline (6, 40 mg, 0.131 mmol) were combined in a mixture of dry chloroform (7 mL) and dry methanol (2 mL). The wine-colored solution was stirred at room temperature for 24 h and diluted with dry 1,2-dichloroethane (4 mL). Sodium triacetoxyborohydride (41 mg, 0.193 mmol) was added in one portion, the solution color changed to pale orange, and the reaction was stirred for an additional 24 h at room temperature. Removal of the solvent and purification by preparative thin-layer chromatography (octadecyl-functionalized silica gel, methanol) afforded chemosensor 7 as a pale red powder (49 mg, 55% yield). $^1$H NMR (d$_7$-dimethylformamide, 300 MHz): δ 8.55 (1 H, d, J=8.5 Hz), 8.35 (1 H, d, J=10.0 Hz), 8.28 (2 H, d, J=8.0 Hz), 8.15 (1 H, d, J=7.0 Hz), 7.75-7.94 (2 H, m), 7.54 (1 H, d, J=7.5 Hz), 7.46-7.50 (1 H, m), 7.42 (2 H, d, J=13.0 Hz), 7.35 (2 H, d, J=12.0 Hz), 7.24 (2 H, dd, $J_1$=23.0 Hz, $J_2$=14.0 Hz), 6.96-7.19 (5 H, m), 6.83 (1 H, d, J=14.5 Hz), 6.49-6.71 (2 H, m), 5.60 (1 H, br s), 4.84 (2 H, br s), 3.50-3.76 (6 H, m). HRMS (ESI) calcd for [M+H]$^+$ 699.2602, found 699.2573. The diacetate derivative, ZNP1-Ac, was prepared by reaction of 7 with acetic anhydride/Cs$_2$CO$_3$ in DMF. HRMS (ESI) calcd for [M+H]$^+$ 783.2819, found 783.2799.

EXAMPLE 7

Spectroscopic Materials and Methods

Millipore water was used to prepare all aqueous solutions, which were passed through 0.2 um cellulose filters prior to use. All spectroscopic measurements were performed under simulated physiological conditions using buffer solutions containing 50 mM HEPES, 4-(2-hydroxyethyl)-1-piperazineethanesulfonic acid, and 100 mM KCl adjusted to pH 7.5. A glass electrode (Orion), calibrated prior to each use, was used to determine solution pH. Solutions of Zn$^{2+}$ were prepared from 100 mM stock solutions of ZnCl$_2$ in water. Absorption spectra were recorded on a Hewlett-Packard 8453A diode array spectrophotometer, and fluorescence spectra on a Photon Technology International (PTI) Quanta Master 4 L-format scanning spectrofluorimeter equipped with an LPS-220B 75-watt xenon lamp and power supply, A-1010B lamp housing with integrated igniter, switchable 814 photon-counting/analog photomultiplier detection unit, and MD-5020 motor driver. Samples for absorption and emission measurements were contained in 1 cm×1 cm quartz cuvettes (3.5 mL volume, Stama). The experiments for measuring quantum yields, apparent dissociation constants ($K_d$), and metal ion selectivities were performed by using standard protocols. Quantum yields were determined by reference to fluorescein in 0.1 N NaOH (Φ=0.95). Confocal fluorescence imaging experiments were performed with a Zeiss LSM510 laser scanning microscopy system containing an Axiovert 200M inverted fluorescence microscope. The microscope was equipped with an argon ion laser (488-nm excitation) and objective lenses (100×), and scanning was performed using the META detection system operating in lambda mode (Zeiss) with 10.7 nm collection windows. During imaging measurements, cell samples were kept on the microscope stage in a CTI-3700 incubator at 37° C. under 5% CO$_2$. Additions of Zn$^{2+}$ as the pyrithione complex (2-mercaptopyridine N-oxide), TPEN [N,N,N',N'-tetra(2-picolyl)ethylenediamine], or SNOC (S-nitrosocysteine) to cell samples were performed directly on the microscope stage by bath application to the media. SNOC was prepared immediately before use.

EXAMPLE 8

2-{11-[(2-{[(2-Ethylsulfanylethyl)pyridin-2-ylmethylamino]methylphenylamino)-methyl]-3-hydroxy-10-oxo-10H-benzo[c]xanthen-7-yl}benzoic acid (10, MS4)

To 4.5 mL of 7:2 CHCl$_3$\MeOH were added 5 (33 mg, 0.081 mmol) and 9 (24 mg, 0.081 mmol), and the resulting purple-brown solution was stirred at room temperature for 24 h. The reaction was diluted with 1 mL of DCE and NaB(OAc)$_3$H (27 mg, 0.13 mmol) was added, and the reaction was stirred for an additional 24 h. The solvents were removed in vacuo and preparative TLC on silica gel (9:1 CHCl$_3$\MeOH) afforded the pure dye as a purple solid (23 mg, 42%). TLC $R_f$=0.55 (9:1 CHCl$_3$\MeOH); mp>325° C., decomp. $^1$H NMR (CD$_3$OD, 300 MHz) δ 0.940 (6H, t), 2.09 (4H, q), 2.26 (2H, q), 2.39 (4H, m), 3.54 (2H, s), 4.68 (2H, q), 6.66 (2H, m), 6.97-7.13 (5H, m), 7.27-7.36 (4H, m), 7.67 (2H, m), 8.15 (1H, d), 8.27 (1H, d).

EXAMPLE 9

2-{11-[(2-{[Bis-(2-ethylsulfanylethyl)amino]methyl}phenylamino)methyl]-3-hydroxy-10-oxo-10H-benzo[c]xanthen-7-yl}benzoic acid (12, MS5)

To 9 mL of 7:2 CHCl$_3$\MeOH were added 5 (71 mg, 0.17 mmol) and 11 (52 mg, 0.17 mmol), which gave a red-brown solution that was stirred at room temperature. After 24 h, 3 mL of DCE and NaB(OAc)$_3$H (40 mg, 0.19 mmol) were added and the reaction was stirred for an additional 24 h, during which time it became wine-colored. The solvents were removed under reduced pressure and preparative TLC on silica gel (20:1 CHCl$_3$\MeOH) yielded pure dye 12 as a purple solid (38 mg, 32%). TLC $R_f$=0.64 (9:1 CHCl$_3$\MeOH). $^1$H NMR (CD$_3$OD, 300 MHz) δ 0.84 (3H, t), 1.92 (2H, q), 2.22-2.46 (4H, m), 3.46-3.65 (4H, m), 4.70 (2H, q), 6.65 (1H, t), 6.73 (1H, d), 6.87 (1H, dd), 7.03-7.11 (3H, m), 7.17 (2H, t), 7.24-7.40 (5H, m), 7.38 (1H, t), 7.60-7.69 (2H, m), 8.15 (1H, d), 8.21 (2H, m).

EXAMPLE 10

Spectroscopic Measurements

Millipore water was used to prepare all aqueous solutions. Buffers (HEPES, CHES) Calbiochem and Puratonic grade KCl was purchased from Calbiochem. Mercury stock solutions (10 mM) were prepared from 99.999% anhydrous HgCl2, purchased from Aldrich, and water. DMSO stock solutions (1 mM) of MS4 and MS5 were prepared, partitioned, stored at −25° C. and thawed in the dark immediately before use. All measurements were conducted in aqueous buffer at pH 8 (50 mM HEPES, 100 mM KCl) or pH 9 (50 mM CHES, 100 mM KCl). Fluorescence spectra were collected by using a Photon Technology International (Lawrenceville, N.J.) Quanta Master 4L-format scanning spectrofluorimeter equipped with an LPS-220B 75-W xenon lamp and power supply, A-1010B lamp housing with integrated igniter, switchable 814 photon-counting/analog PMT detector, and a MD-5020 motor driver. Optical absorption spectroscopy was performed by using a Cary 1E double-beam scanning spectrophotometer. All samples were contained in 3 mL quartz cuvettes (Stama) and maintained at 25° C. by means of a circulating water bath.

REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Frederickson et al. *J. Neurosci. Meth.* 1987, 20, 91-103; Zalewski et al. *Biochem. J.* 1993, 296, 403-408; Mahadevan et al. *Aust. J. Chem.* 1996, 49, 561-568; Budde et al. *Neuroscience* 1997, 79, 347-358; Canzoniero et al. *Neurobiology of Disease* 1997, 4, 275-279; Fahrni et al. *J. Am. Chem. Soc.* 1999, 121, 11448-11458; Nasir et al. *JBIC* 1999, 4, 775-783; Belgodere et al. *Heterocycles* 1985, 23, 349-354; Romary et al. *J. Chem. Soc (C)* 1968, 2884-2887; da Mota et al. *J. Chem. Soc.* (A) 1969, 2036-2042; Hörlein, U. *Chemische Berichte* 1954, 87, 463-472; Houser et al. *J. Am. Chem. Soc.* 1995, 117, 10745-10746; Kovacs, Z.; Sherry, A. D. *Tet. Lett.* 1995, 51, 9269-9272; Prasad et al. *J. Chem. Soc. Perkin Trans.* 1991, 3329-3332; Vallee et al. *Physiol. Rev.* 1993, 73: 79-118; Lippard et al. *Principles of Bioinorganic Chemistry;* 1st ed.; University Science Books: Mill Valley, 1994; Frederickson, C. *Int. Rev. Neurobiol.* 1989, 31: 145-238

Huang, E. *Proc. Natl. Acad. Sci. U.S.A.* 1997, 94: 13386-13387; Nasir, et al. *JBIC* 1999, 4: 775-783; Frederickson et al. *Biol. Signals* 1994, 3: 127-139; Budde et al. *Neuroscience* 1997, 79: 347-358; Harrison et al. *Neuropharmacology* 1994, 33: 935-952; Choi et al. *Ann. Rev. Neurosci.* 1998, 21: 347-375; Cuajungco et al. *Neurobiology of Disease* 1997, 4: 137-169; Palmiter et al. *EMBO J.* 1995, 14: 639-649; Palmiter, et al. *EMBO J.* 1996, 15: 1784-1791; Palmiter, et al. *Proc. Natl. Acad. Sci. USA* 1996, 93: 14934-14939; Ebadi, et al. *Methods Enzymol.* 1991, 205: 363-387; Ebadi, et al. *Neurochem. Int.* 1995, 27: 1-22; Ebadi, et al. *J. Neurochem.* 1996, 66: 2121-2127; Evans, I. *J. Org Chem.* 1959, 24: 863; Palmiter, et al. *Proc. Natl. Acad. Sci. USA* 1992, 89: 6333-6337; Pountney, et al. *FEBS Lett.* 1994, 345: 193-197; Tsuji, et al. *EMBO J.* 1992, 11: 4843-4850; Uchida, et al. *Neuron* 1991, 7: 337-347; Slomianka, L. *Neuroscience* 1992: 48, 325-352; Atar, et al. *J. Biol. Chem.* 1995, 270: 2473-2477; de Silva et al. *Chem. Rev.* 1997, 97: 1515-1566; Tsien, R. Y. *Fluorescent and Photochemical Probes of Dynamic Biochemical Signals Inside Living Cells;* Czarnik, A. W., Ed.; American Chemical Society: Washington D.C., 1993; Vol. 538, pp 130-146.; Czarnik, A. W. *Curr. Biol.* 1995, 2: 423-428; Frederickson, et al. *J. Neurosci. Meth.* 1987, 20: 91-103; Walkup et al. *J. Am. Chem Soc.* 2000, 122: 5644-5645;

Lakowicz, J. R. *Principles of Fluorescence Spectroscopy;* 2nd ed.; Kluwe Academic/Plenum: New York, 1999; Gruenwedel, D. W. *Inorg. Chem.* 1968, 7: 495-501; SMART; 5.05 ed.; Bruker AXS, Inc.: Madison, Wis., 1998; Feig et al. *Inorg. Chem.* 1996, 25: 6892-6898; McBryde, W. A. E. *Talanta* 1974, 21: 979-1004; Walkup et al. *J. Am. Chem Soc.* 2000: 122: S1-S7; Burton et al. *J. Soc. Chem. Ind. London* 1948: 67: 345; Wolf, H. U. *Experientia* 1973, 29: 241-249; Anderegg et al. *Helv. Chim. Acta* 1977, 60: 123-140; Sen, et al. *J. Indian Chem. Soc.* 1929, 6, 505.

Sen, et al. *J. Indian Chem. Soc.* 1929, 6, 51; Job, A., *Ann. Chem.* (Paris) 1928, 9, 113-203; U.S. Pat. No. 6,013,802; U.S. Pat. No. 6,083,758; U.S. Pat. No. 6,063,637; U.S. Pat. No. 5,986,094; U.S. Pat. No. 5,756,771; U.S. Pat. No. 4,510,251; Vallee, B. L. & Falchuk, K. H. (1993) Physiol. Rev. 73, 79-118; Berg, J. M. & Shi, Y. (1996) Science 271, 1081-1085; Coleman, J. E. (1998) Curr. Opin. Chem. Biol. 2, 222-234; O'Halloran, T. V. (1993) Science 261, 715-724; Ho, E. & Ames, B. N. (2002) Proc. Natl. Acad. Sci. USA 99, 16770-16775; Daiyasu, H., Osaka, K., Ishino, Y. & Toh, H. (2001) FEBS Lett. 503, 1-6; Truong-Tran, A. Q., Carter, J., Ruffin, R. E. & Zalewski, P. D. (2001) BioMetals 14, 315-330; Finney, L. A. & O'Halloran, T. V. (2003) Science 300, 931-936; Frederickson, C. J. (1989) Int. Rev. Neurobiol. 31, 145-238; Zalewski, P. D., Millard, S. H., Forbes, I. J., Kapaniris, O., Slavotinek, A., Betts, W. H., Ward, A. D., Lincoln, S. F. & Mahadevan, I. (1994) J. Histochem. Cytochem. 42, 877-884; Sorenson, M. B., Stoltenberg, M., Juhl, S., Danscher, G. & Ernst, E. (1997) Prostate 31, 125-130; Suh, S. W., Jensen, K. B., Jensen, M. S., Silva, D. S., Kesslak, P. J., Danscher, G. & Frederickson, C. J. (2000) Brain Res. 852, 274-278; Chausmer, A. B. (1998) J. Am. Coll. Nutr. 17, 109-115; Henshall, S. M., Afar, D. E. H., Rasiah, K. K., Horvath, L. G., Gish, K., Caras, I., Ramakrishnan, V., Wong, M., Jeffry, U., Kench, J. G., Quinn, D. I., Turner, J. J., Delprado, W., Lee, C.-S., Golovsky, D., Brenner, P. C., O'Neill, G. F., Kooner, R., Stricker, P. D., Grygiel, J. J., Mack, D. H. & Sutherland, R. L. (2003) Oncogene 22, 6005-6012; MacDiarmid, C. W., Milanick, M. A. & Eide, D. J. (2003) J. Biol. Chem. 278, 15065-15072; Tsien, R. W. & Tsien, R. Y. (1990) Annu. Rev. Cell Biol. 6, 715-760; Godwin, H. A. & Berg, J. M. (1996) J. Am. Chem. Soc. 118, 6514-6515; Walkup, G. K. & Imperiali, B. (1996) J. Am. Chem. Soc. 118, 3053-3054; Shults, M. D., Pearce, D. A. & Imperiali, B. (2003) J. Am. Chem. Soc. 125, 10591-10597; Thompson, R. B., Cramer, M. L., Bozym, R. & Fierke, C. A. (2002) J. Biomed. Optics 7, 555-560; Barondeau, D. P., Kassman, C. J., Tainer, J. A. & Getzoff, E. D. (2002) J. Am. Chem. Soc. 124, 3522-3524; Walkup, G. K., Burdette, S. C., Lippard, S. J. & Tsien, R. Y. (2000) J. Am. Chem Soc. 122, 5644-5645; Burdette, S. C., Walkup, G. K., Spingler, B., Tsien, R. Y. & Lippard, S. J. (2001) J. Am. Chem. Soc. 123, 7831-7841; Burdette, S. C. & Lippard, S. J. (2001) Coord. Chem. Rev. 216-217, 333-361; Chang, C. J., Nolan, E. M., Jaworski, J., Burdette, S. C., Sheng, M. & Lippard, S. J. (2004) Chem. Biol. 11, in press; Gee, K. R., Zhou, Z. L., Ton-That, D., Sensi, S. L. & Weiss, J. H. (2002) Cell Calcium 31, 245-251; Hirano, T., Kikuchi, K., Urano, Y. & Nagano, T. (2002) J. Am. Chem. Soc. 124, 6555-6562.; Lim, N. C., Yao, L., Freake, H. C. & Brückner, C. (2003) Bioorg. Med. Chem. Lett. 13, 2251-2254; Kimber, M. C., Mahadevan, I. B., Lincoln, S. F., Ward, A. D. & Tiekink, E. R. T. (2000) J. Org. Chem. 65, 8204-8209; Burdette, S. C., Frederickson, C. J., Bu, W. & Lippard, S. J. (2003) J. Am. Chem. Soc. 125, 1778-1787; Gee, K. R., Zhou, Z.-L., Qian, W.-J. & Kennedy, R. (2002) J. Am. Chem. Soc. 124, 776-778; Maruyama, S., Kikuchi, K., Hirano, T., Urano, Y. & Nagano, T. (2002) J. Am. Chem. Soc. 124, 10650-10651; Henary, M. M. & Fahrni, C. J. (2002) J. Phys. Chem. A 106, 5210-5220; Taki, M., Wolford, J. L. & O'Halloran, T. V., (2004) J. Am. Chem. Soc. 126, in press; Woodroofe, C. C. & Lippard, S. J. (2003) J. Am. Chem. Soc. 125, 11458-11459; Pangborn, A. B., Giardello, M. A., Grubbs, R. H., Rosen, R. K. & Timmers, F. J. (1996) Organomet. 15, 1518-1520; Brannon, J. H. & Magde, D. (1978) J. Phys. Chem. 82, 705-709; Qian, W.-J., Gee, K. R. & Kennedy, R. T. (2003) Anal. Chem. 75, 3468-3475; Kröncke, K.-D. & Kolb-Bachofen, V. (1999) Methods Enzymol. 301, 126-135; Smith, G. A., Metcalfe, J. C. & Clarke, S. D. (1993) J. Chem. Soc. Perkin Trans. 2, 1195-1204; Spahl, D. U., Berendji-Grün, D., Suschek, C. V., Kolb-Bachofen, V. & Kröncke, K.-D. (2003) Proc. Natl. Acad. Sci. USA 100, 13952-13957; Gryglewski, R. J. & Minuz, P. (2000) in NATO Science Series (IOS Press, Amsterdam; Washington, D.C.), Vol. 317; Gu, Z., Kaul, M., Yan, B., Kridel, S. J., Cui, J., Strongin, A., Smith, J. W., Liddington, R. C. & Lipton, S. A. (2002) Science 297, 1186-1190; Berendji, D., Kolb-Bachofen, V., Meyer, K. L., Grapenthin, O., Weber, H., Wahn, V. & Kröncke, K.-D. (1997) FEBS Lett. 405, 37-41; Chen, Y., Irie, Y., Keung, W. M. & Maret, W. (2002) Biochemistry 41, 8360-8367; Pearce, L. L., Wasserloos, K., Croix, C. M. S., Gandley, R., Levitan, E. S. & Pitt, B. R. (2000) J. Nutr. 130, 1467S-1470S; Kröncke, K.-D., Fehsel, K., Schmidt, T., Zenke, F. T., Dasting, F., Wesener, J. R., Bettermann, H., Breunig, K. D. & Kolb-Bachofen, V. (1994) Biochem. Biophys. Res. Commun. 200, 1105-1110; U.S. Pat. No. 6,013,802; U.S. Pat. No. 6,083,758; U.S. Pat. No. 6,063,637; U.S. Pat. No. 5,986,094; U.S. Pat. No. 5,756,771; U.S. Pat. No. 4,510,251; and U.S. patent application Ser. No. 09/901,466, filed Jul. 9, 2001, Ser. No. 10/124,742, filed Apr. 17, 2002, Ser. No. 10/429,898, filed May 4, 2003, and 60/537,121, filed Jan. 19, 2004.

EQUIVALENTS

The invention now being fully described, it will be apparent to one of ordinary skill in the art that many changes and modifications may be made thereto without requiring more than routine experimentation or departing from the spirit or scope of the appended claims.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

What is claimed is:

1. A naphthofluorescein-based ligand, of the following structure:

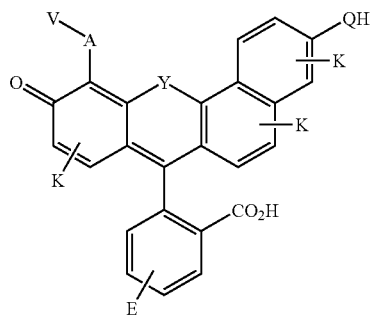

wherein, independently for each occurrence:

A is a chemical moiety selected from the group consisting of —$CH_2$—, —C(=O)—, —C(=S)—, and —C(H)=;

Q is O;

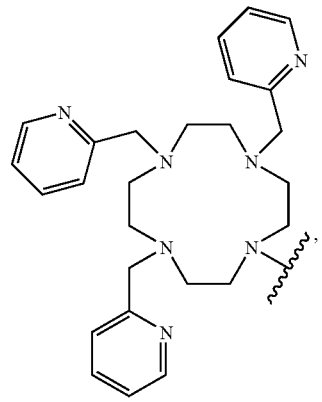

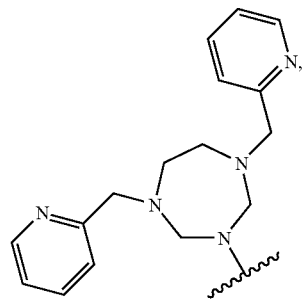

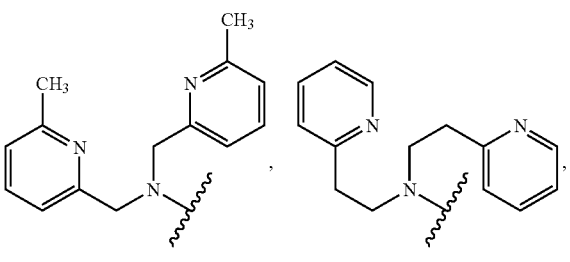

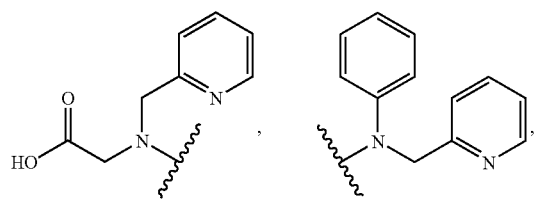

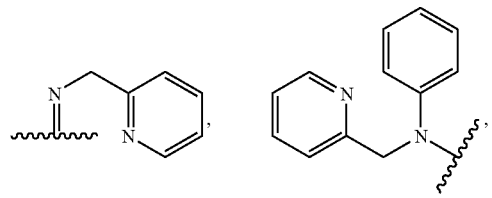

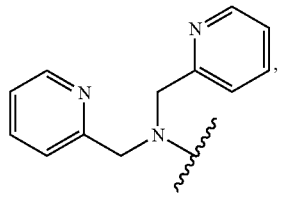

-continued
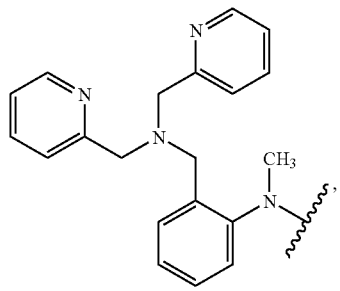
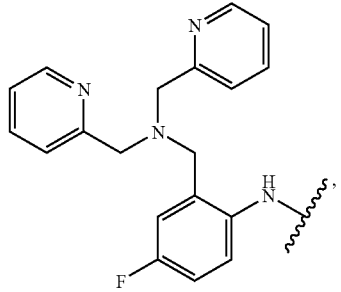
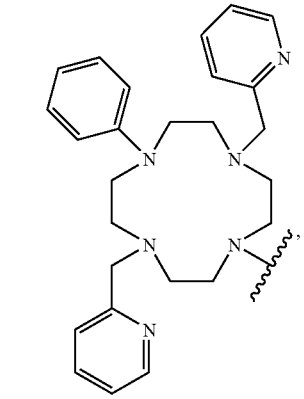
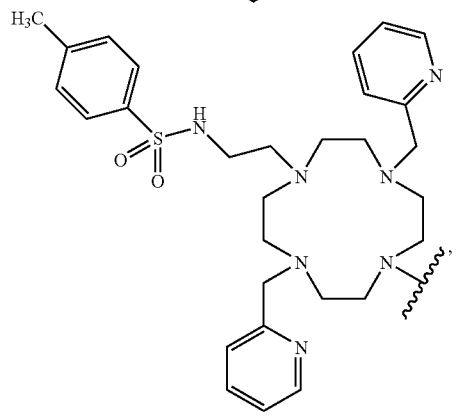

-continued

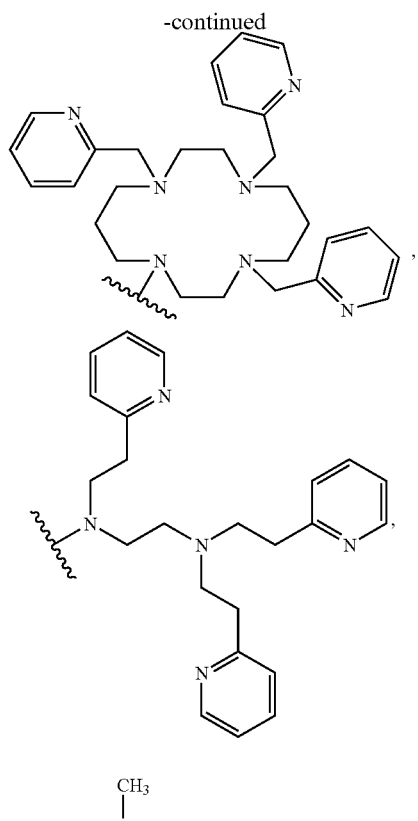

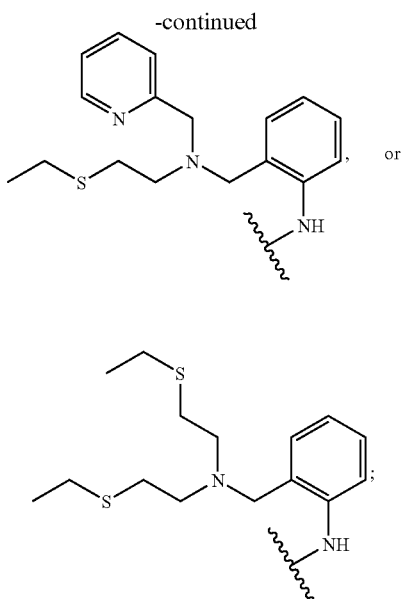

Y is O;
K is hydrogen; and
E is hydrogen.

2. The naphthofluorescein-based ligand of claim 1, wherein A is —CH$_2$—.

3. The naphthofluorescein-based ligand of claim 1, wherein said ligand forms a tridentate or tetradentate chelating agent upon said complexation.

4. The naphthofluorescein-based ligand of claim 1, wherein said ligand has the following structure:

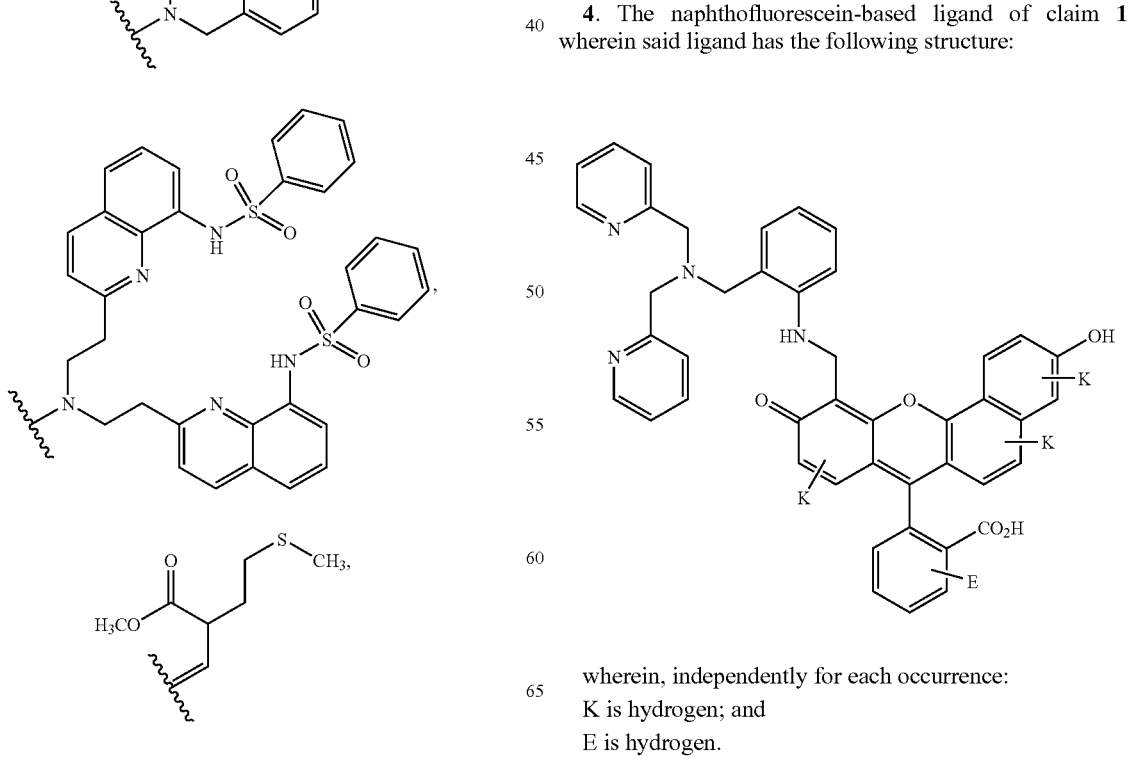

wherein, independently for each occurrence:
K is hydrogen; and
E is hydrogen.

5. The naphthofluorescein-based ligand of claim 1, wherein said ligand has the following structure:

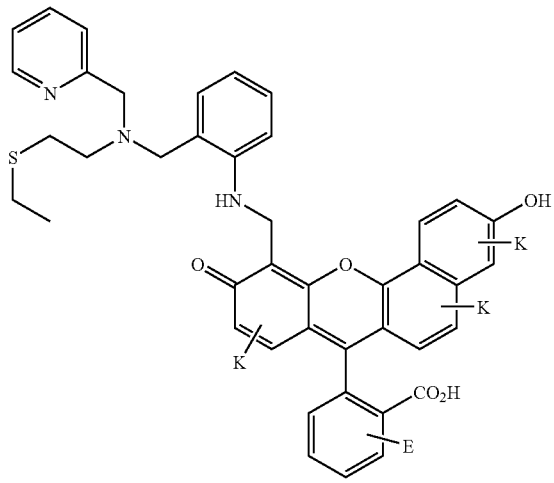

wherein, independently for each occurrence:
K is hydrogen; and
E is hydrogen.

6. The naphthofluorescein-based ligand of claim 1, wherein said ligand has the following structure:

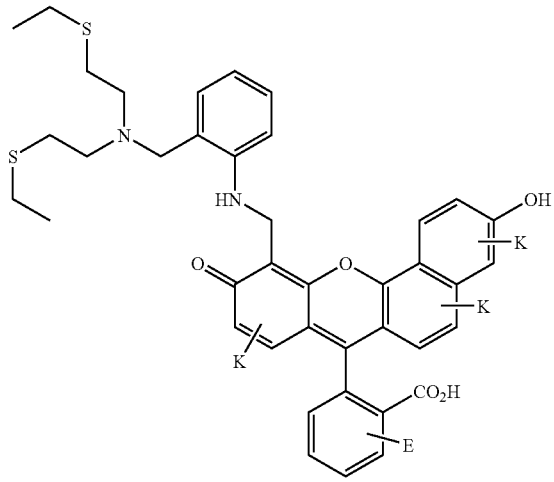

wherein, independently for each occurrence:
K is hydrogen; and
E is hydrogen.

7. A coordination complex, comprising a metal ion coordinated to the naphthofluorescein-based ligands of any one of claims 2, 3, 4, 5, and 6.

8. The coordination complex of claim 7, wherein the metal ion is $Zn^{2+}$.

9. The coordination complex of claim 7, wherein the metal ion is $Hg^{2+}$.

10. A naphthofluorescein-based scaffold, comprising a scaffold having the following structure:

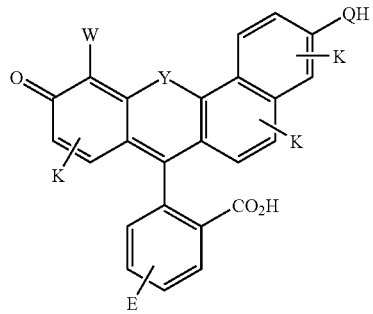

wherein, independently for each occurrence:
Q is O;
Y is O;
W comprises one of the following: —$CH_2X$, —C(O)H, —C(O)$OR_2$, or —C(O)OH, wherein X is halogen, hydroxyl, amine, or thiol, and $R_2$ is alkyl;
K is hydrogen; and
E is hydrogen.

11. The naphthofluorescein-based scaffold of claim 10, wherein said scaffold has one of the following structures:

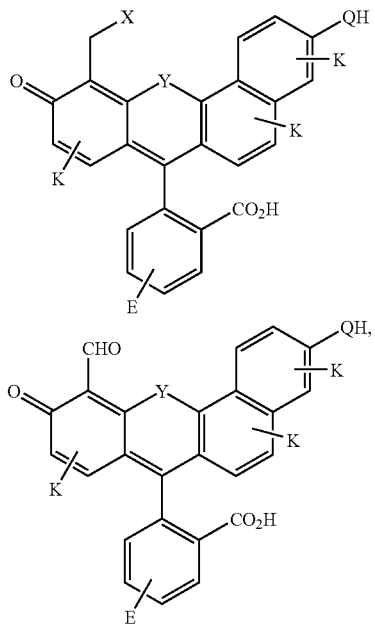

wherein X is halogen, hydroxyl, amine, or thiol.

* * * * *

UNITED STATES PATENT AND TRADEMARK OFFICE
CERTIFICATE OF CORRECTION

Page 1 of 1

PATENT NO.      : 7,488,820 B2
APPLICATION NO. : 11/039396
DATED           : February 10, 2009
INVENTOR(S)     : Stephen J. Lippard et al.

It is certified that error appears in the above-identified patent and that said Letters Patent is hereby corrected as shown below:

In column 1, lines 15-16, replace:

"The subject invention was made in part with support from the U.S. Government."

with

--This invention was made with government support under grant number R01 GM065519 awarded by the National Institutes of Health. The government has certain rights in this invention.--

Signed and Sealed this
Twelfth Day of July, 2011

David J. Kappos
*Director of the United States Patent and Trademark Office*